(12) United States Patent
Pasquet et al.

(10) Patent No.: US 8,936,779 B2
(45) Date of Patent: Jan. 20, 2015

(54) COSMETIC COMPOSITION COMPRISING AT LEAST ONE CATIONIC POLY(VINYLLACTAM), AT LEAST ONE FATTY ALCOHOL AND AT LEAST ONE AMINO SILICONE, COSMETIC PROCESS AND USE OF THE COMPOSITION

(75) Inventors: Dorothee Pasquet, Bois Colombes (FR); Cecile Bebot, Asnieres (FR)

(73) Assignee: L'Oreal, Paris (FR)

( * ) Notice: Subject to any disclaimer, the term of this patent is extended or adjusted under 35 U.S.C. 154(b) by 1080 days.

(21) Appl. No.: 11/643,864

(22) Filed: Dec. 22, 2006

(65) Prior Publication Data

US 2007/0190016 A1 Aug. 16, 2007

Related U.S. Application Data

(60) Provisional application No. 60/761,330, filed on Jan. 24, 2006.

(30) Foreign Application Priority Data

Dec. 22, 2005 (FR) ...................................... 05 13194

(51) Int. Cl.
| | | |
|---|---|---|
| A61Q 5/02 | (2006.01) | |
| A61Q 5/06 | (2006.01) | |
| A61Q 5/12 | (2006.01) | |
| A61K 8/81 | (2006.01) | |

(52) U.S. Cl.
CPC .. *A61Q 5/12* (2013.01); *A61Q 5/06* (2013.01); *A61K 8/8182* (2013.01)
USPC ..................................................... 424/70.122

(58) Field of Classification Search
CPC .......... A61K 8/8182; A61Q 5/06; A61Q 5/12
See application file for complete search history.

(56) References Cited

U.S. PATENT DOCUMENTS

| | | | |
|---|---|---|---|
| 4,956,430 A | 9/1990 | Tazi | |
| 6,071,499 A * | 6/2000 | Dupuis | 424/47 |
| 6,121,373 A * | 9/2000 | Starch | 524/837 |
| 6,451,747 B1 * | 9/2002 | Decoster | 510/119 |
| 7,066,966 B2 | 6/2006 | Cottard et al. | |
| 7,204,861 B2 * | 4/2007 | Marsh et al. | 8/405 |
| 7,323,015 B2 | 1/2008 | Cottard et al. | |
| 7,410,505 B2 | 8/2008 | Cottard et al. | |
| 2003/0147842 A1 | 8/2003 | Restle et al. | |
| 2004/0115156 A1 * | 6/2004 | De La Mettrie et al. | 424/70.15 |
| 2004/0131572 A1 | 7/2004 | Cottard et al. | |
| 2004/0131576 A1 | 7/2004 | Decoster et al. | |
| 2004/0133993 A1 | 7/2004 | Cottard et al. | |
| 2004/0133994 A1 | 7/2004 | Cottard et al. | |
| 2004/0163187 A1 | 8/2004 | Cottard et al. | |
| 2004/0205901 A1 | 10/2004 | Cottard et al. | |
| 2005/0169869 A1 * | 8/2005 | Laurent et al. | 424/70.13 |
| 2005/0220723 A1 * | 10/2005 | Benabdillah et al. | 424/47 |
| 2005/0235431 A9 | 10/2005 | Cottard et al. | |

FOREIGN PATENT DOCUMENTS

| | | |
|---|---|---|
| EP | 1 378 226 A1 | 1/2004 |
| EP | 1 413 288 A1 | 4/2004 |
| EP | 1 426 038 A1 | 6/2004 |
| EP | 1 600 150 A1 | 11/2005 |
| FR | 2 831 800 A1 | 5/2003 |
| FR | 2 845 908 A1 | 4/2004 |
| WO | WO 00/68282 | 11/2000 |
| WO | WO 02/058647 A1 | 8/2002 |
| WO | WO 02/058648 A1 | 8/2002 |
| WO | WO 02/096381 A1 | 12/2002 |

OTHER PUBLICATIONS

Parchem MSDS Data sheet for cetyl steary alcohol, revised Jul. 7, 2009.*
French Search Report for FR 0513194, dated Oct. 12, 2006.
English language Derwent Abstract of EP 1 600 150 A1 , Nov. 30, 2005.
French Search Report for Application No. FR 0513195, dated Oct. 12, 2006.
Co-pending U.S. Appl. No. 11/643,861.
Office Action issued in U.S. Appl. No. 11/643,861, dated Oct. 28, 2009.
Office Action issued in U.S. Appl. No. 11/643,861, dated Oct. 28, 2010.

\* cited by examiner

*Primary Examiner* — Suzanne Ziska
(74) *Attorney, Agent, or Firm* — The Marbury Law Group, PLLC

(57) ABSTRACT

The present disclosure relates to a cosmetic composition for treating keratin fibers, including human keratin fibers such as the hair, comprising, in a cosmetically acceptable medium, at least one cationic poly(vinyllactam) polymer, at least one fatty alcohol and at least one amino silicone.

43 Claims, No Drawings

COSMETIC COMPOSITION COMPRISING AT LEAST ONE CATIONIC POLY(VINYLLACTAM), AT LEAST ONE FATTY ALCOHOL AND AT LEAST ONE AMINO SILICONE, COSMETIC PROCESS AND USE OF THE COMPOSITION

This application claims benefit of priority under 35 U.S.C. §119 to French Patent Application No. FR 05 13194, filed Dec. 22, 2005, the contents of which are also incorporated herein by reference.

The present disclosure relates to a cosmetic composition for treating keratin fibers, including human keratin fibers such as the hair, comprising at least one cationic poly(vinyllactam) polymer, at least one fatty alcohol and at least one amino silicone, to a haircare use of this composition, a cosmetic treatment process using it, and also a device containing this composition.

The hair is generally damaged and embrittled by the action of external atmospheric agents such as light and bad weather, and by mechanical and/or chemical treatments, such as brushing, combing, bleaching, permanent-waving and/or dyeing. As a result, the hair can often be difficult to manage, and can be difficult to disentangle or style, and heads of hair, and densely populated heads of hair, present difficulty in conserving an attractive style due to the fact that the hair lacks vigor.

In order to overcome this, it is now common practice to apply to the hair haircare products comprising conditioning agents that facilitate the disentangling and combing of wet hair, which can provide good hold of the hairstyle and can give the hair, after drying, softness, body, volume and elasticity.

Thus, these haircare products generally can make it possible to tame the hair, to make it smooth and to reduce the volume of frizzy hair, i.e., the volume of hair that is undesirably frizzy in the form of small ringlets, thus making the hair easier to style.

These hair compositions are often formulated using fatty alcohols and frequently comprise cationic surfactants as conditioning agents.

However, although the cationic silicones conventionally used in these hair compositions may generally give good cosmetic properties, these silicones cannot sufficiently tame frizzy hair or satisfactorily control its volume.

There is thus a real need to find cosmetic compositions, such as for caring for or styling the hair, which may allow the taming of frizzy hair or to control its volume, while at the same time allowing the hair to have satisfactory cosmetic properties, such as in terms of softness, disentangling, appearance and feel.

The inventors have discovered, surprisingly and unexpectedly, that by combining at least one cationic poly(vinyllactam) polymer, at least one fatty alcohol and at least one amino silicone, it is possible to obtain cosmetic compositions that make it possible to tame, smooth out and reduce the volume of frizzy hair, while at the same time giving the hair good cosmetic properties, such as in terms of softness, disentangling and feel.

Accordingly, one aspect of the present disclosure relates to a cosmetic composition for treating keratin fibers, including human keratin fibers such as the hair, comprising such a combination.

Another aspect of the present disclosure relates to the use of the cosmetic composition according to the disclosure for haircare.

The present disclosure also relates to a cosmetic treatment process using the cosmetic composition according to the disclosure.

Still another aspect of the present disclosure relates to an aerosol device comprising the composition according to the disclosure.

Other subjects, characteristics, aspects and benefits of the present disclosure will emerge even more clearly upon reading the description and the examples that follow.

According to at least one embodiment of the present disclosure, the cosmetic composition for treating keratin fibers, including human keratin fibers such as the hair, comprises, in a cosmetically acceptable medium:

at least one cationic poly(vinyllactam) polymer comprising:
  a) at least one monomer chosen from vinyllactam and alkylvinyllactam monomers;
  b) at least one monomer chosen from formulae (Ia) and (Ib):

$$CH_2 = C(R_1) - CO - X - (Y)_p - (CH_2 - CH_2 - O)_m - (CH_2 - CH(R_2) - O)_n - (Y_1)_q - \overset{R_{3+}}{\underset{R_5}{N}} - R_4 \quad Z^- \quad (Ia)$$

$$CH_2 = C(R_1) - CO - X - (Y)_p - (CH_2 - CH_2 - O)_m - (CH_2 - CH(R_2) - O)_n - (Y_1)_q - N\overset{R_3}{\underset{R_4}{\diagdown}} \quad (Ib)$$

wherein:
X is chosen from an oxygen atom and radicals $NR_6$,
$R_1$ and $R_6$, independently of each other, are chosen from hydrogen atoms and linear and branched $C_1$-$C_5$ alkyl radicals,
$R_2$ is chosen from linear and branched $C_1$-$C_4$ alkyl radicals,
$R_3$, $R_4$ and $R_5$, independently of each other, are chosen from hydrogen atoms, linear and branched $C_1$-$C_{30}$ alkyl radicals and radicals of formula (II):

$$-(Y_2)_r-(CH_2-CH(R_7)-O)_x-R_8 \quad (II)$$

Y, $Y_1$ and $Y_2$, independently of each other, are chosen from linear and branched $C_2$-$C_{16}$ alkylene radicals,
$R_7$ is chosen from a hydrogen atom, linear and branched $C_1$-$C_4$ alkyl radicals, and linear and branched $C_1$-$C_4$ hydroxyalkyl radicals,
$R_8$ is chosen from a hydrogen atom and linear and branched $C_1$-$C_{30}$ alkyl radicals,
p, q and r, independently of each other, are either the value 0 or the value 1, m and n, independently of each other, are integers ranging from 0 to 100, x is an integer ranging from 1 to 100, and Z is chosen from organic and mineral acid anions;

with the proviso that:
at least one of the substituents $R_3$, $R_4$, $R_5$ or $R_8$ is chosen from linear and branched $C_9$-$C_{30}$ alkyl radicals,
if m or n is other than zero, then q is equal to 1, and
if m or n is equal to zero, then p or q is equal to 0;
at least one fatty alcohol, and
at least one amino silicone.

The cationic poly(vinyllactam) polymers used in the cosmetic composition according to at least one embodiment of the present disclosure comprise:
a) at least one monomer chosen from vinyllactam and alkylvinyllactam monomers;
b) at least one monomer chosen from formulae (Ia) and (Ib):

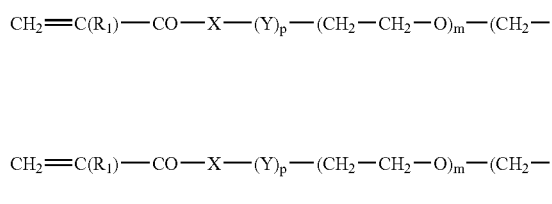

wherein:

X is chosen from an oxygen atom and radicals $NR_6$, $R_1$ and $R_6$, independently of each other, are chosen from hydrogen atoms and linear and branched $C_1$-$C_5$ alkyl radicals, $R_2$ is chosen from linear and branched $C_1$-$C_4$ alkyl radicals, $R_3$, $R_4$ and $R_5$, independently of each other, are chosen from hydrogen atoms, linear and branched $C_1$-$C_{30}$ alkyl radicals, and radicals of formula (II):

$$-(Y_2)_r-(CH_2-CH(R_7)-O)_x-R_8 \qquad (II)$$

Y, $Y_1$ and $Y_2$, independently of each other, are chosen from linear and branched $C_2$-$C_{16}$ alkylene radicals, $R_7$ is chosen from a hydrogen atom, linear and branched $C_1$-$C_4$ alkyl radicals, and linear and branched $C_1$-$C_4$ hydroxyalkyl radicals, $R_8$ is chosen from a hydrogen atom and linear and branched $C_1$-$C_{30}$ alkyl radicals, p, q and r, independently of each other, are either the value 0 or the value 1, m and n, independently of each other, are integers ranging from 0 to 100, x is an integer ranging from 1 to 100, and Z is chosen from organic and mineral acid anions;

with the proviso that:
at least one of the substituents $R_3$, $R_4$, $R_5$ or $R_8$ is chosen from linear and branched $C_9$-$C_{30}$ alkyl radicals,
if m or n is other than zero, then q is equal to 1, and
if m or n is equal to zero, then p or q is equal to 0.

The cationic poly(vinyllactam) polymers used in the cosmetic composition according to at least one embodiment of the present disclosure may be crosslinked or noncrosslinked and may also be block polymers.

In at least one embodiment, the counterion $Z^-$ of the monomers of formula (Ia) is chosen from halide ions, phosphate ions, the methosulfate ion and the tosylate ion.

According to at least one embodiment, $R_3$, $R_4$ and $R_5$, independently of each other, are chosen from hydrogen atoms and linear and branched $C_1$-$C_{30}$ alkyl radicals.

In at least one embodiment, the at least one monomer b) is a monomer of formula (Ia) for which, in at least one further embodiment, m and n are equal to 0.

The at least one monomer chosen from vinyllactam and alkylvinyllactam monomers used according to at least one embodiment is a compound of formula (III):

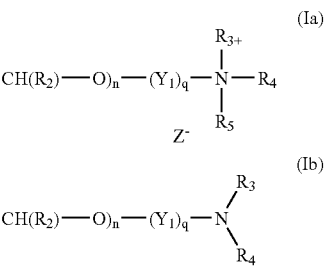

wherein:

s is an integer ranging from 3 to 6, $R_9$ is chosen from a hydrogen atom and $C_1$-$C_5$ alkyl radicals, and $R_{10}$ is chosen from a hydrogen atom and $C_1$-$C_5$ alkyl radicals;

with the proviso that at least one of the radicals $R_9$ and $R_{10}$ is a hydrogen atom.

In at least one further embodiment, the monomer (III) is vinylpyrrolidone.

The cationic poly(vinyllactam) polymers used in the composition according to at least one embodiment of the present disclosure may also contain at least one additional monomer, such as cationic or nonionic monomers.

As compounds that are used according to at least one embodiment of the present disclosure, non-limiting mention may be made of the following terpolymers comprising:
(a) at least one monomer of formula (III),
(b) at least one monomer of formula (Ia) wherein p=1, q=0, $R_3$ and $R_4$, independently of each other, are chosen from hydrogen atoms and $C_1$-$C_5$ alkyl radicals and $R_5$ is chosen from $C_9$-$C_{24}$ alkyl radicals, and
(c) at least one monomer of formula (Ib) wherein $R_3$ and $R_4$, independently of each other, are chosen from hydrogen atoms and $C_1$-$C_5$ alkyl radicals.

In at least one embodiment, terpolymers comprising, by weight, 40% to 95% of monomer (a), 0.1% to 55% of monomer (c) and 0.25% to 50% of monomer (b) are used.

Such polymers are described in International Patent Application No. WO 00/68282, the content of which is incorporated herein.

As cationic poly(vinyllactam) polymers according to at least one embodiment of the present disclosure, vinylpyrrolidone/dimethylaminopropylmethacrylamide/dodecyldimethylmethacrylamidopropylammonium tosylate terpolymers, vinylpyrrolidone/dimethylaminopropylmethacrylamide/cocoyldimethylmethacrylamidopropylammonium tosylate terpolymers, vinylpyrrolidone/dimethylaminopropylmethacrylamide/lauryldimethylmethacrylamidopropylammonium tosylate or chloride terpolymers are used.

The weight-average molecular mass of the cationic poly(vinyllactam) polymers according to at least one embodiment of the present disclosure ranges from 500 to 20,000,000. For example, the weight-average molecular mass may range from 200,000 to 2,000,000 or from 400,000 to 800,000.

One polymer that is used according to at least one embodiment is the polymer sold under the name Styleze W20 by the company ISP, which is a terpolymer of vinylpyrrolidone/dimethylaminopropylmethacrylamide and of lauryldimethylmethacrylamidopropylammonium chloride.

In at least one embodiment, the at least one cationic poly(vinyllactam) polymer is present in the cosmetic composition according to the present disclosure in an amount ranging from 0.05% to 30% by weight, such as from 0.1% to 15% by weight or from 0.2% to 10% by weight, relative to the total weight of the composition.

For the purposes of the present disclosure, the term "fatty alcohol" means any saturated or unsaturated, linear or branched pure fatty alcohol containing at least 8 carbon atoms.

The at least one fatty alcohol may not be oxyalkylenated or glycerolated.

The at least one fatty alcohol may have the structure R—OH wherein R is chosen from saturated and unsaturated, linear and branched radicals containing from 8 to 40 carbon atoms, such as from 8 to 30 carbon atoms. In at least one embodiment, R is chosen from $C_{12}$-$C_{24}$ alkyl and $C_{12}$-$C_{24}$ alkenyl groups. R may be substituted with at least one hydroxyl group.

Non-limiting examples of fatty alcohols that may be mentioned include lauryl alcohol, cetyl alcohol, stearyl alcohol, oleyl alcohol, behenyl alcohol, linoleyl alcohol, undecylenyl alcohol, palmitoleyl alcohol, arachidonyl alcohol and erucyl alcohol, and mixtures thereof.

The at least one fatty alcohol may represent a mixture of fatty alcohols, which means that several species of fatty alcohol may coexist, in the form of a mixture, in a commercial product.

Fatty alcohol mixtures that may be used in at least one embodiment include cetylstearyl alcohol and cetearyl alcohol.

In at least one embodiment, the at least one non-oxyalkylenated fatty alcohol is solid or pasty at a temperature of 25° C. For the purposes of the present disclosure, the expression "fatty alcohol that is solid or pasty at 25° C." means a fatty alcohol that has a viscosity, measured with a rheometer at a shear rate of 1 s$^{-1}$, of greater than or equal to 1 Pa·s.

According to at least one embodiment, the at least one fatty alcohol used in the cosmetic composition according to the present disclosure is chosen from cetyl alcohol and cetearyl alcohol.

The at least one fatty alcohol may be present in the composition in an amount ranging from 0.1% to 30%, such as from 0.2% to 20% or from 0.5% to 10% by weight, relative to the total weight of the composition.

The cosmetic composition according to the present disclosure also comprises at least one amino silicone.

As used herein, the term "silicone" means, in accordance with what is generally accepted, any organosilicone polymer or oligomer of linear or cyclic, branched or crosslinked structure, of variable molecular weight, obtained by polymerization and/or polycondensation of suitably functionalized silanes, and consisting essentially of a repetition of main units in which the silicon atoms are linked together via oxygen atoms (siloxane bond —Si—O—Si—), optionally substituted hydrocarbon-based radicals being directly linked via a carbon atom to the silicon atoms. The hydrocarbon-based radicals that are the most common are alkyl radicals, such as $C_1$-$C_{10}$, and, for example, methyl, fluoroalkyl radicals, the alkyl part of which is of $C_1$-$C_{10}$, and aryl radicals, such as phenyl.

For the purposes of the present disclosure, the term "amino silicone" means any silicone comprising at least one primary, secondary or tertiary amine functional group or a quaternary ammonium group.

The at least one amino silicone used in the cosmetic composition according to the disclosure is chosen from:

(a) the compounds of formula (V):

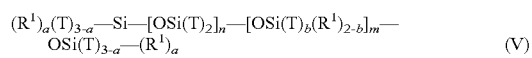

(V)

wherein:

T is chosen from a hydrogen atom and phenyl, hydroxyl (—OH), and $C_1$-$C_8$ alkyl radicals, such as methyl, and $C_1$-$C_8$ alkoxy radicals, such as methoxy, a is an integer from 0 to 3, such as 0, b is 0 or 1, such as, for example, 1, m and n are numbers such that the sum (n+m) can range from 1 to 2000, such as from 50 to 150, wherein n may be a number from 0 to 1999, such as from 49 to 149, and m may be a number from 1 to 2000, such as from 1 to 10;

$R^1$ is chosen from monovalent radicals of formula —$C_qH_{2q}$L wherein q is a number from 2 to 8 and L is an optionally quaternized amino group chosen from the following groups:

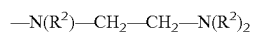

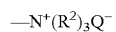

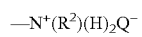

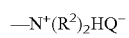

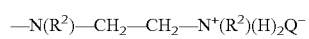

wherein $R^2$ is chosen from a hydrogen atom, phenyl, benzyl aand saturated monovalent hydrocarbon-based radicals, for example a $C_1$-$C_{20}$ alkyl radical, and Q$^-$ is a halide ion such as, for example, fluoride, chloride, bromide or iodide.

In at least one embodiment, the amino silicones corresponding to the definition of formula (V) are chosen from the compounds of following formula (IV):

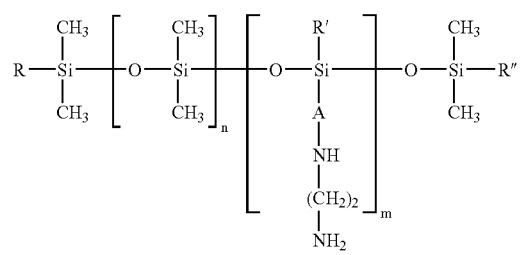

(IV)

wherein:

R, R' and R", which may be identical or different, are chosen from $C_1$-$C_4$ alkyl radicals, such as $CH_3$; $C_1$-$C_4$ alkoxy radicals, such as methoxy; and OH;

A is chosen from linear and branched, $C_3$-$C_8$ alkylene radicals, such as $C_3$-$C_6$ alkylene radicals;

m and n are integers dependent on the molecular weight and whose sum ranges from 1 to 2000.

According to at least one embodiment, R, R' and R", which may be identical or different, are chosen from $C_1$-$C_4$ alkyl and hydroxyl radicals, A is a $C_3$ alkylene radical and m and n are such that the weight-average molecular mass of the compound ranges from 5000 to 500,000. Compounds of this type are referred to in the CTFA dictionary as "amodimethicones."

According to at least one embodiment, R, R' and R", which may be identical or different, are chosen from $C_1$-$C_4$ alkoxy and hydroxyl radicals, wherein at least one of the radicals R or R" is an alkoxy radical and A is a $C_3$ alkylene radical. The hydroxyl/alkoxy molar ratio according to at least one embodiment ranges from 0.2/1 to 0.4/1, such as equal to 0.3/1. Moreover, m and n are such that the weight-average molecular mass of the compound range from 2000 to $10^6$. In at least one further embodiment, n ranges from 0 to 999 and m ranges from 1 to 1000, and the sum of n and m ranges from 1 to 1000.

In this category of compounds, non-limiting mention may be made, inter alia, of the product Belsil® ADM 652 sold by Wacker.

According to at least one embodiment, R and R", which are different, are chosen from $C_1$-$C_4$ alkoxy and hydroxyl radicals, wherein at least one of the radicals R or R" is an alkoxy radical, R' is a methyl radical and A is a $C_3$ alkylene radical. The hydroxyl/alkoxy molar ratio according to at least one embodiment ranges from 1/0.8 to 1/1.1, such as equal to 1/0.95. In at least one embodiment, m and n are such that the weight-average molecular mass of the compound ranges from 2000 to 200,000. In at least one further embodiment, n ranges from 0 to 999 and m ranges from 1 to 1000, the sum of n and m ranging from 1 to 1000.

In at least one embodiment, non-limiting mention may be made of the product Fluid WR® 1300 sold by the company Wacker.

According to at least one embodiment, R and R" are hydroxyl radicals, R' is a methyl radical and A is chosen from $C_4$-$C_8$ alkylene radicals, such as a $C_4$ alkylene radical. In at least one embodiment, m and n are such that the weight-average molecular mass of the compound ranges from 2000 to $10^6$. In at least one further embodiment, n ranges from 0 to 1999 and m ranges from 1 to 2000, and the sum of n and m ranges from 1 to 2000.

A product of this type is sold, for example, under the name DC 28299 by Dow Corning.

The molecular mass of these silicones is determined by gel permeation chromatography (ambient temperature, polystyrene standard; μ styragem columns; eluent THF; flow rate 1 mm/m; 200 μl of a solution containing 0.5% by weight of silicone are injected into THF and detection is performed by UV refractometry).

A product corresponding to the definition of formula (V) is, for example, the polymer known in the CTFA dictionary as "trimethylsilyl amodimethicone," corresponding to formula (VI) below:

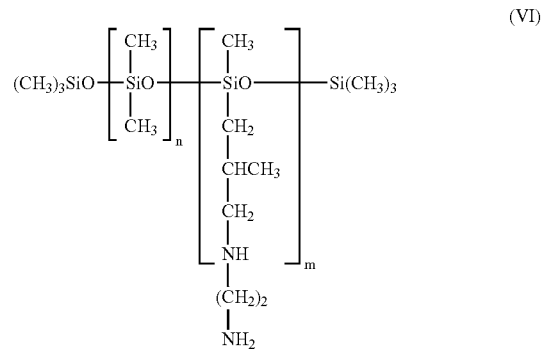

wherein n and m have the meanings given above in accordance with formula (V).

Such compounds are described, for example, in European Patent Application No. EP-A-95238; a compound of formula (VI) is sold, for example, under the name Q2-8220 by the company OSI.

(b) the compounds of formula (VII):

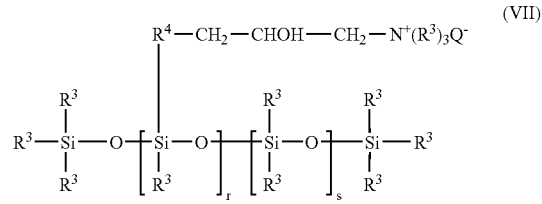

wherein:

$R^3$ is chosen from monovalent $C_1$-$C_{18}$ hydrocarbon-based radicals, such as $C_1$-$C_{18}$ alkyl or $C_2$-$C_{18}$ alkenyl radicals, for example methyl, $R^4$ is chosen from divalent hydrocarbon-based radicals, such as $C_1$-$C_{18}$ alkylene radicals and divalent $C_1$-$C_{18}$ alkyleneoxy radicals, for example $C_1$-$C_8$ alkyleneoxy radicals;

$Q^-$ is a halide ion, such as chloride;

r has an average statistical value from 2 to 20, such as from 2 to 8;

s has an average statistical value from 20 to 200, such as from 20 to 50.

Such compounds are described, for example, in U.S. Pat. No. 4,185,087.

A compound falling within this class is the product sold by the company Union Carbide under the name Ucar Silicone ALE 56.

(c) the quaternary ammonium silicones of formula (XII):

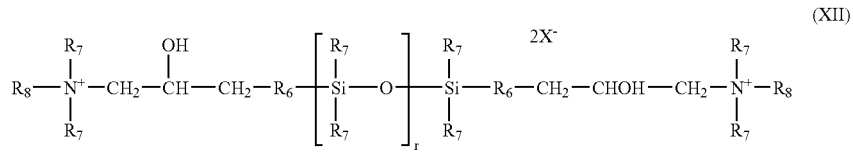

wherein:
R$_7$, which may be identical or different, is chosen from monovalent hydrocarbon-based radicals containing from 1 to 18 carbon atoms, such as C$_1$-C$_{18}$ alkyl radicals, including methyl, C$_2$-C$_{18}$ alkenyl radicals and rings containing 5 or 6 carbon atoms;

R$_6$ is chosen from divalent hydrocarbon-based radicals, such as C$_1$-C$_{18}$ alkylene radicals and divalent C$_1$-C$_{18}$ alkyleneoxy radicals, for example C$_1$-C$_8$ alkyleneoxy radicals, linked to the Si via an SiC bond;

R$_8$, which may be identical or different, is chosen from a hydrogen atom, monovalent hydrocarbon-based radicals containing from 1 to 18 carbon atoms, and C$_1$-C$_{18}$ alkyl radicals, C$_2$-C$_{18}$ alkenyl radicals and radicals —R$_6$—NHCOR$_7$;

X$^-$ is chosen from anions such as halide ions, including chloride, and organic acid salts (acetate, etc.);

r has a mean statistical value from 2 to 200, such as from 5 to 100.

These silicones are described, for example, in European Patent Application No. EP-A 0 530 974.

(d) the amino silicones of formula (XIII):

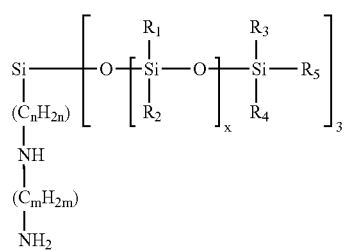

(XIII)

wherein:
R$_1$, R$_2$, R$_3$ and R$_4$, which may be identical or different, are chosen from C$_1$-C$_4$ alkyl radicals and phenyl groups,
R$_5$ is chosen from C$_1$-C$_4$ alkyl radicals and a hydroxyl group,
n is an integer ranging from 1 to 5,
m is an integer ranging from 1 to 5, and
wherein x is chosen such that the amine number ranges from 0.01 to 1 meq/g.

The amino silicones that are used in accordance with at least one embodiment of the present disclosure are polysiloxanes containing amine groups such as amodimethicones or trimethylsilylamodimethicones (CTFA, 4th edition, 1997), such as silicones containing quaternary ammonium groups. When these compounds are used, at least one embodiment involves their combined use with cationic and/or nonionic surfactants.

By way of non-limiting example, it is possible to use the product sold under the name Cationic Emulsion DC 929 by the company Dow Corning, which comprises, besides amodimethicone, a cationic surfactant comprising a mixture of products corresponding to the formula:

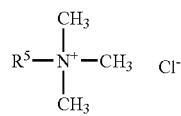

wherein R$^5$ is chosen from C$_{14}$-C$_{22}$ alkenyl and/or alkyl radicals derived from tallow fatty acids, and known under the CTFA name tallowtrimonium chloride, in combination with a nonionic surfactant of formula:

C$_9$H$_{19}$—C$_6$H$_4$—(OC$_2$H$_4$)$_{10}$—OH, known under the CTFA name as Nonoxynol 10.

Use may also be made, by way of non-limiting example, of the product sold under the name Cationic Emulsion DC 939 by the company Dow Corning, which comprises, besides amodimethicone, a cationic surfactant which is trimethylcetylammonium chloride and a nonionic surfactant of formula:

C$_{13}$H$_{27}$—(OC$_2$H$_4$)$_{12}$—OH, known under the CTFA name trideceth-12.

Another commercial product that may be used according to at least one embodiment of the present disclosure is the product sold under the name Dow Corning Q2 7224 by the company Dow Corning, comprising, in combination, the trimethylsilyl amodimethicone described above, a nonionic surfactant of formula:

C$_8$H$_{17}$—C$_6$H$_4$—(OCH$_2$CH$_2$)$_{40}$—OH, known under the CTFA name octoxynol-40, a second nonionic surfactant of formula: C$_{12}$H$_{25}$—(OCH$_2$—CH$_2$)$_6$—OH, known under the CTFA name isolaureth-6, and propylene glycol.

The at least one amino silicone may be present in the cosmetic composition in an amount ranging from 0.01% to 20%, such as from 0.05% to 10% or from 0.1% to 5% by weight, relative to the total weight of the cosmetic composition.

In at least one embodiment, the cationic polyvinyllactam/fatty alcohol weight ratio ranges from 0.1 to 5, the cationic polyvinyllactam/amino silicone weight ratio ranges from 0.1 to 5, and the fatty alcohol/amino silicone weight ratio ranges from 0.5 to 10.

The cosmetic composition may also comprise at least one oxyalkylenated silicone or at least one silicone chosen from silicone gums.

For the purposes of the present disclosure, the term "oxyalkylenated silicone" means any silicone comprising at least one oxyalkylene group of the type (—C$_x$H$_{2x}$O—)$_a$ in which x ranges from 2 to 6 and a is greater than or equal to 2.

The at least one oxyalkylenated silicone that may be used in the cosmetic composition as disclosed herein can be chosen from those of formulae (XIV), (XV), (XVI), (XVII) and (XVIII):

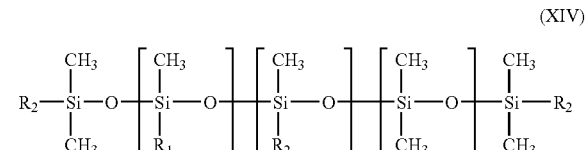

(XIV)

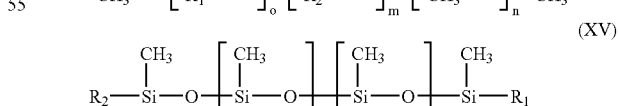

(XV)

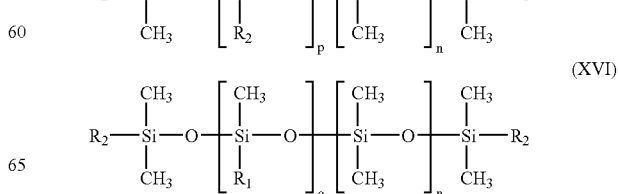

(XVI)

-continued

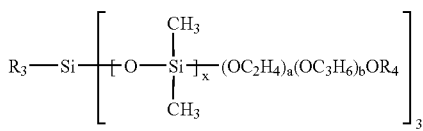

(XVII)

wherein:
- $R_1$, which may be identical or different, is chosen from linear and branched $C_1$-$C_{30}$ alkyl and phenyl radicals,
- $R_2$, which may be identical or different, is chosen from radicals —$C_cH_{2c}$—O—$(C_2H_4O)_a(C_3H_6O)_b$—$R_5$ and radicals —$C_cH_{2c}$—O—$(C_4H_8O)_a$—$R_5$,
- $R_3$ and $R_4$, which may be identical or different, are chosen from linear and branched $C_1$ to $C_{12}$ alkyl radicals, such as a methyl radical,
- $R_5$, which may be identical or different, is chosen from a hydrogen atom, linear and branched alkyl radicals containing from 1 to 12 carbon atoms, linear and branched alkoxy radicals containing from 1 to 6 carbon atoms, linear and branched acyl radicals containing from 2 to 30 carbon atoms, a hydroxyl radical, —$SO_3M$ radicals, $C_1$-$C_6$ aminoalkoxy radicals optionally substituted on the amine, $C_2$-$C_6$ aminoacyl radicals optionally substituted on the amine, —$NHCH_2CH_2COOM$ radicals, —$N(CH_2CH_2COOM)_2$ radicals, aminoalkyl radicals optionally substituted on the amine and on the alkyl chain, $C_2$-$C_{30}$ carboxyacyl radicals, groups optionally substituted with one or two substituted aminoalkyl radicals, —$CO(CH_2)_dCOOM$ radicals, —$COCHR_7(CH_2)_d$ COOM radicals, —$NHCO(CH_2)_dOH$ radicals, —$NH_3Y$ radicals, and phosphate groups,
- M, which may be identical or different, is chosen from hydrogen, Na, K, Li, $NH_4$ and organic amines,
- $R_7$ is chosen from a hydrogen atom and radicals —$SO_3M$,
- d ranges from 1 to 10,
- m ranges from 0 to 20,
- n ranges from 0 to 500,
- o ranges from 0 to 20,
- p ranges from 1 to 50,
- a ranges from 0 to 50,
- b ranges from 0 to 50,
- a+b is greater than or equal to 2,
- c ranges from 0 to 4,
- x ranges from 1 to 100,
- Y is chosen from monovalent minerals and organic anions such as halide (chloride or bromide), sulfate or carboxylate (acetate, lactate or citrate), with the proviso that when the silicone is of formula (XV) with $R_5$ denoting hydrogen, then n is greater than 12.

Such silicones are sold, for example, by the company Goldschmidt under the trade names Abil WE 09, Abil EM 90, Abil B8852, Abil B8851, Abil B8843 and Abil B8842, by the company Dow Corning under the names Fluid DC 190, DC3225 C, Q2-5220, Q25354 and Q2-5200, by the company Rhodia Chimie under the names Silbione Oil 70646 and Rhodorsil Oil 10634, by the company General Electric under the names SF1066 and SF1188, by the company SWS Silicones under the name Silicone Copolymer F 754, by the company Amerchol under the name Silsoft Beauty Aid SL, by the company Shin-Etsu under the name KF 351, by the company Wacker under the name Belsil DMC 6038, by the company Siltech under the names Silwax WD-C, Silwax WD-B, Silwax WD-IS, Silwax WSL, Silwax DCA 100 and Siltech Amine 65, by the company Fanning Corporation under the names Fancorsil SLA and Fancorsil LIM1, and by the company Phoenix under the name Pecosil.

These silicones are described, for example, in U.S. Pat. Nos. 5,070,171; 5,149,765; 5,093,452 and 5,091,493.

At least one polyoxyalkylenated silicone chosen from those of formulae (XV) and (XVI) are used according to at least one embodiment. In at least one further embodiment, these formulae satisfy at least one, or possibly all, of the following conditions:
- c is equal to 2 or 3,
- $R_1$ is a methyl radical,
- $R_5$ is chosen from a methyl radical and $C_{12}$-$C_{22}$ acyl radicals, $CO(CH_2)_dCOOM$,
- a ranges from 2 to 25, such as from 2 to 15,
- b is equal to 0,
- n ranges from 0 to 100,
- p ranges from 1 to 20.

The polyoxyalkylenated silicones according to the disclosure may also be chosen from the silicones of formula (XVIII):

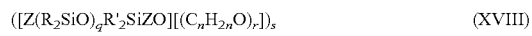

(XVIII)

wherein formula (XVIII):
- $R_2$ and $R'_2$, which may be identical or different, are chosen from monovalent $C_1$-$C_{30}$ hydrocarbon-based radicals,
- n is an integer ranging from 2 to 4,
- q is a number greater than or equal to 4, such as a number ranging from 4 to 200 or from 4 to 100,
- r is a number greater than or equal to 4, such as a number ranging from 4 to 200 or from 5 to 100,
- s is a number greater than or equal to 4, such as from 4 to 1000 or from 5 to 300,
- Z is chosen from divalent organic groups linked to the adjacent silicon atom via a carbon-silicon bond and to the polyoxyalkylene block $(C_nH_{2n}O)$ via an oxygen atom,
- the average molecular weight of each siloxane block ranges from 400 to 10,000, the average molecular weight of each polyoxyalkylene block ranges from 300 to 10,000,
- the siloxane blocks are present in an amount ranging from 10% to 95% by weight of the block copolymer,
- the number-average molecular weight of the block copolymer ranges from 2500 to 1,000,000, such as from 3000 to 200,000 or from 6000 to 100,000.

In at least one embodiment, $R_2$ and $R'_2$ are chosen from linear and branched alkyl radicals, for instance methyl, ethyl, propyl, butyl, pentyl, hexyl, octyl, decyl and dodecyl radicals; aryl radicals, for instance phenyl and naphthyl; aralkyl and alkylaryl radicals, for instance benzyl and phenylethyl; and tolyl and xylyl radicals.

In at least one embodiment, Z is chosen from —R"—, —R"—CO—, —R"—NHCO—, —R"—NH—CO—NH—R'"— or —R"—OCONH—R'"—NHCO—, wherein R" is chosen from linear and branched $C_1$-$C_6$ divalent alkylene groups, for instance ethylene, propylene or linear or branched butylene, and R'" is chosen from divalent alkylene groups and divalent arylene groups, for instance —$C_6H_4$—, —$C_6H_4$—$C_6H_4$—, —$C_6H_4$—$CH_2$—$C_6H_4$— or —$C_6H_4$—$C(CH_3)_2$ $C_6H_4$—.

In at least one further embodiment, Z is chosen from divalent alkylene radicals, such as linear and branched —$C_3H_6$— radicals and —$C_4H_8$— radicals.

The preparation of the block copolymers used in the context of the present disclosure is described in European Patent Application No. EP 0 492 657 A1, the teaching of which is incorporated in the present disclosure.

Such products are sold, for example, under the name Silicone Fluid FZ-2172 by the company OSI.

The silicones that are used in the cosmetic compositions according to at least one embodiment of the present disclosure may be in the form of aqueous solutions or optionally in the form of aqueous dispersions or emulsions.

In at least one embodiment, the at least one silicone that may be used in the cosmetic composition may also be chosen from silicone gums.

The silicone gums that may be used in the cosmetic composition according to at least one embodiment of the present disclosure are polydiorganosiloxanes having high number-average molecular masses ranging from 200,000 to 1,000,000, used alone or as a mixture in at least one solvent. The at least one solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane.

Non-limiting mention may be made of the following products:
  polydimethylsiloxane,
  polydimethylsiloxane/methylvinylsiloxane gums,
  polydimethylsiloxane/diphenylsiloxane,
  polydimethylsiloxane/phenylmethylsiloxane,
  polydimethylsiloxane/diphenylsiloxane/methylvinylsiloxane.

Products that can be used according to at least one embodiment are mixtures such as:
  mixtures formed from a polydimethylsiloxane hydroxylated at the end of the chain, or dimethiconol (CTFA) and from a cyclic polydimethylsiloxane also called cyclomethicone (CTFA), such as the product Q2 1401 sold by the company Dow Corning;
  mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500,000, dissolved in the oil SF 1202 Silicone Fluid corresponding to decamethylcyclopentasiloxane;
  mixtures of two PDMSs of different viscosities, for example a PDMS gum and a PDMS oil, such as the product SF 1236 from the company General Electric. The product SF 1236 is a mixture of an SE 30 gum defined above, having a viscosity of 20 m²/s, and an SF 96 oil, with a viscosity of $5 \times 10^{-6}$ m²/s. This product may contain 15% SE 30 gum and 85% SF 96 oil.

The cosmetic composition may also comprise at least one additional fixing polymers.

For the purposes of the present disclosure, the term "fixing polymer" means any polymer that makes it possible to impart a given shape or to maintain a given shape or hairstyle.

The at least one fixing polymer that may be used in the cosmetic composition according to at least one embodiment of the present disclosure is chosen from cationic, anionic, amphoteric and nonionic polymers.

For the purposes of the present disclosure, the term "cationic polymer" means any polymer comprising cationic groups and/or groups that may be ionized into cationic groups.

The cationic fixing polymers that may be used in the cosmetic composition according to at least one embodiment of the present disclosure are chosen from polymers comprising primary, secondary, tertiary and/or quaternary amine groups forming part of the polymer chain or directly attached thereto, and having a number average molecular weight ranging from 500 to 5,000,000, such as from 1000 to 3,000,000.

Among these polymers, non-limiting mention may be made of the following cationic polymers:
  (1) homopolymers or copolymers derived from acrylic or methacrylic esters or amides with amine functional groups, and comprising at least one of the units of the following formulae:

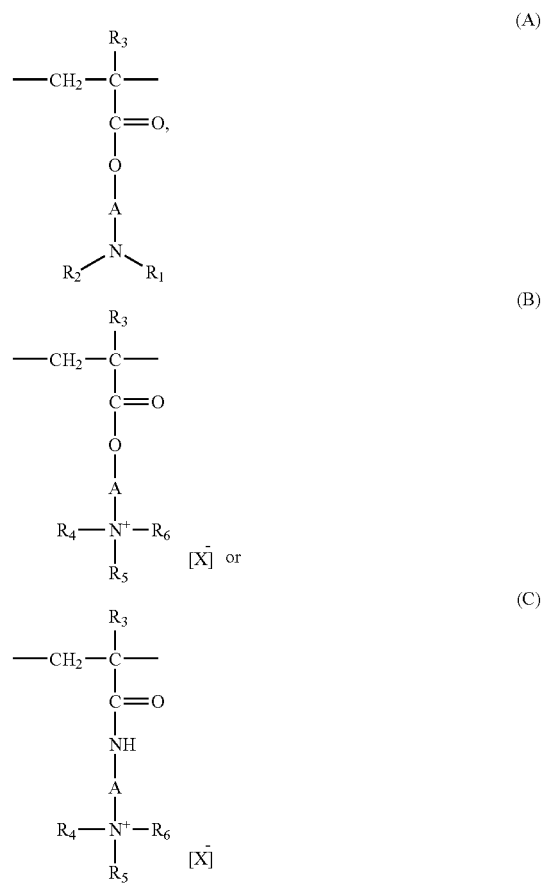

wherein:
  $R_1$ and $R_2$, which may be identical or different, are chosen from hydrogen atoms and alkyl groups having from 1 to 6 carbon atoms;
  $R_3$ is chosen from a hydrogen atom and a group $CH_3$;
  A is chosen from linear and branched alkyl groups comprising 1 to 6 carbon atoms and hydroxyalkyl groups comprising 1 to 4 carbon atoms;
  $R_4$, $R_5$ and $R_6$, which may be identical or different, are chosen from alkyl groups having from 1 to 18 carbon atoms and benzyl groups;
  X is a methosulfate anion or a halide such as chloride or bromide.

The copolymers of the family (1) also contain at least one comonomer unit that may be chosen from acrylamides, methacrylamides, diacetone acrylamides, acrylamides and methacrylamides substituted on the nitrogen with lower ($C_1$-$C_4$) alkyl groups, groups derived from acrylic or methacrylic acids or esters thereof, vinyllactams such as vinylpyrrolidone or vinylcaprolactam, and vinyl esters.

Thus, among these copolymers of the family (1), non-limiting mention may be made of:
  copolymers of acrylamide and of dimethylaminoethyl methacrylate quaternized with dimethyl sulfate or with a dimethyl halide, such as the one sold under the name Hercofloc® by the company Hercules, copolymers of acrylamide and of methacryloyloxyethyltrimethylammonium chloride, described, for example, in European Patent Application No. EP-A-080 976 and sold under the name Bina Quat P 100 by the company Ciba Geigy, copolymers of acrylamide and of methacryloyloxyethyltrimethylammonium methosulfate, such as the product sold under the name Reten by the company Hercules, quaternized or non-quaternized vinylpyrrolidone/dialkylaminoalkyl acrylate or methacrylate copolymers, such as the products sold under the name Gafquat® by the company ISP, such as, for example, Gafquat® 734 or Gafquat® 755, or alternatively the products known as Copolymer® 845, 958 and 937. These polymers are described in detail in French Patent Nos. 2 077 143 and 2 393 573, dimethylaminoethyl methacrylate/vinylcaprolactam/vinylpyrrolidone terpolymers, such as the product sold under the name Gaffix® VC 713 by the company ISP, and quaternized vinylpyrrolidone/dimethylaminopropylmethacrylamide copolymers, such as the product sold under the name Gafquat® HS 100 by the company ISP;

(2) cationic polysaccharides, including those containing quaternary ammonium, such as those described in U.S. Pat. Nos. 3,589,578 and 4,031,307, such as guar gums containing trialkylammonium cationic groups. Such products are sold, for example, under the trade names Jaguar C13S, Jaguar C15 and Jaguar C17 by the company Meyhall;

(3) quaternary copolymers of vinylpyrrolidone and of vinylimidazole;

(4) chitosans or salts thereof; the salts that can be used are, for example, chitosan acetate, lactate, glutamate, gluconate or pyrrolidonecarboxylate. Among these compounds, non-limiting mention may be made of chitosan having a degree of deacetylation of 90.5% by weight, sold under the name Kytan Brut Standard by the company Aber Technologies, and chitosan pyrrolidonecarboxylate sold under the name Kytamer® PC by the company Amerchol.

(5) cationic cellulose derivatives such as copolymers of cellulose or of cellulose derivatives grafted with a water-soluble monomer comprising a quaternary ammonium, and disclosed, for example, in U.S. Pat. No. 4,131,576, such as hydroxyalkylcelluloses, for instance hydroxymethyl-, hydroxyethyl- or hydroxypropylcelluloses grafted, for example, with a methacryloyloxyethyltrimethylammonium, methacrylamidopropyltrimethylammonium or dimethyldiallylammonium salt. The products sold corresponding to this definition are, for example, the products sold under the name Celquat L 200 and Celquat H 100 by the company National Starch.

The anionic fixing polymers generally used are polymers comprising groups derived from carboxylic acid, sulfonic acid or phosphoric acid and have a number average molecular weight ranging from 500 to 5,000,000.

The carboxylic groups are provided by unsaturated monocarboxylic or dicarboxylic acid monomers such as those of formula:

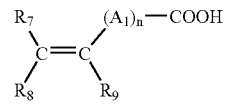

wherein n is an integer ranging from 0 to 10, $A_1$ is a methylene group, optionally connected to the carbon atom of the unsaturated group, or to the neighboring methylene group when n is greater than 1, via a hetero atom such as oxygen or sulfur, $R_7$ is chosen from a hydrogen atom and phenyl and benzyl groups, $R_8$ is chosen from a hydrogen atom and lower alkyl and carboxyl groups, $R_9$ is chosen from a hydrogen atom, lower alkyl groups, $—CH_2—COOH$ groups, phenyl groups and benzyl groups.

In at least one embodiment of the abovementioned formula, a lower alkyl group is a group having 1 to 4 carbon atoms, such as methyl and ethyl.

The anionic fixing polymers containing carboxylic groups that are used according to at least one embodiment of the present disclosure are:

A) acrylic or methacrylic acid homo- or copolymers, or salts thereof, such as the products sold under the names Versicol® E or K by the company Allied Colloid and Ultrahold® by the company BASF, the copolymers of acrylic acid and of acrylamide sold in the form of their sodium salts under the names Reten 421, 423 or 425 by the company Hercules, the sodium salts of polyhydroxycarboxylic acids.

B) copolymers of acrylic or methacrylic acid with a monoethylenic monomer such as ethylene, styrene, vinyl esters, acrylic or methacrylic acid esters, optionally grafted onto a polyalkylene glycol such as polyethylene glycol and optionally crosslinked. Such polymers are described, for example, in French Patent No. 1 222 944 and German Patent Application No. 2 330 956, the copolymers of this type comprising an optionally N-alkylated and/or hydroxyalkylated acrylamide unit in their chain as described, for example, in Luxembourg Patent Application Nos. 75370 and 75371 or sold under the name Quadramer by the company American Cyanamid. Non-limiting mention may also be made of methacrylic acid/ethyl acrylate/tert-butyl acrylate terpolymers such as the product sold under the name Luvimer® 100 P by the company BASF.

Non-limiting mention may also be made of methacrylic acid/acrylic acid/ethyl acrylate/methyl methacrylate copolymers as an aqueous dispersion, sold under the name Amerhold® DR 25 by the company Amerchol.

C) crotonic acid copolymers, such as those comprising vinyl acetate or propionate units in their chain and optionally other monomers such as allylic esters or methallylic esters, vinyl ether or vinyl ester of a linear or branched saturated carboxylic acid with a long hydrocarbon chain such as those containing at least 5 carbon atoms, it being possible for these polymers optionally to be grafted or crosslinked, or alternatively another vinyl, allylic or methallylic ester monomer of an α- or β-cyclic carboxylic acid. Such polymers are described, for example, in French Patent Nos. 1 222 944, 1 580 545, 2 265 782, 2 265 781, 1 564 110 and 2 439 798. Commercial products falling into this class are the resins 28-29-30, 26-13-14 and 28-13-10 sold by the company National Starch.

D) copolymers derived from $C_4$-$C_8$ monounsaturated carboxylic acids or anhydrides chosen from:

copolymers comprising (i) at least one maleic, fumaric or itaconic acid or anhydride and (ii) at least one monomer chosen from vinyl esters, vinyl ethers, vinyl halides, phenylvinyl derivatives, acrylic acid and its esters, the anhydride functional groups of these copolymers optionally being monoesterified or monoamidated. Such polymers are described, for example, in U.S. Pat. Nos. 2,047,398; 2,723,248; and 2,102,113; and British Patent No. GB 839 805, and including those sold under the names Gantrez® AN or ES by the company ISP, copolymers comprising (i) at least one maleic, citraconic or itaconic anhydride unit and (ii) at least one monomer chosen from allylic and methallylic esters optionally comprising at least one acrylamide, methacrylamide, α-olefin, acrylic or methacrylic ester, acrylic or methacrylic acid or vinylpyrrolidone groups in their chain, the anhydride functional groups of these copolymers optionally being monoesterified or monoamidated.

These polymers are described, for example, in French Patent Nos. FR 2 350 384 and FR 2 357 241.

E) polyacrylamides comprising carboxylate groups.

The homopolymers and copolymers comprising sulfonic groups are polymers comprising vinylsulfonic, styrenesulfonic, naphthalenesulfonic or acrylamidoalkylsulfonic units.

These polymers can be chosen, for example, from:

polyvinylsulfonic acid salts having a molecular weight ranging from 1000 to 100,000, as well as the copolymers with an unsaturated comonomer such as acrylic or methacrylic acids and their esters, as well as acrylamide or its derivatives, vinyl ethers and vinylpyrrolidone;

polystyrenesulfonic acid salts such as the sodium salts that are sold under the names Flexan® 500 and Flexan® 130 by National Starch. These compounds are described in French Patent No. FR 2 198 719;

polyacrylamidesulfonic acid salts, such as those mentioned in U.S. Pat. No. 4,128,631, and, for example, polyacrylamidoethylpropanesulfonic acid sold under the name Cosmedia Polymer HSP 1180 by Henkel.

In at least one embodiment, the anionic fixing polymers are chosen from acrylic acid copolymers, such as the acrylic acid/ethyl acrylate/N-tert-butylacrylamide terpolymers sold, for example, under the name Ultrahold® Strong by the company BASF, copolymers derived from crotonic acid, such as vinyl acetate/vinyl tert-butylbenzoate/crotonic acid terpolymers and the crotonic acid/vinyl acetate/vinyl neododecanoate terpolymers sold, for example, under the name Resin 28-29-30 by the company National Starch, polymers derived from maleic, fumaric or itaconic acids or anhydrides with vinyl esters, vinyl ethers, vinyl halides, phenylvinyl derivatives and acrylic acid and esters thereof, such as the methyl vinyl ether/monoesterified maleic anhydride copolymers sold, for example, under the name Gantrez® by the company ISP, the copolymers of methacrylic acid and of methyl methacrylate sold under the name Eudragit® L by the company Rohm Pharma, the copolymers of methacrylic acid and of ethyl acrylate sold under the name Luvimer® MAEX or MAE by the company BASF, the vinyl acetate/crotonic acid copolymers sold under the name Luviset CA 66 by the company BASF, the vinyl acetate/crotonic acid copolymers grafted with polyethylene glycol sold under the name Aristoflex A® by the company BASF.

Among the anionic fixing polymers mentioned above, at least one embodiment of the present disclosure may use the methyl vinyl ether/monoesterified maleic anhydride copolymers sold under the name Gantrez® ES 425 by the company ISP, the acrylic acid/ethyl acrylate/N-tert-butylacrylamide terpolymers sold under the name Ultrahold® Strong by the company BASF, the copolymers of methacrylic acid and of methyl methacrylate sold under the name Eudragit® L by the company Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, and the copolymers of methacrylic acid and of ethyl acrylate sold under the name Luvimer® MAEX or MAE by the company BASF.

The amphoteric fixing polymers that can be used in accordance with the present disclosure can be chosen from polymers comprising units B and C distributed randomly in the polymer chain, wherein B is a unit derived from a monomer comprising at least one basic nitrogen atom and C is a unit derived from an acid monomer comprising one or more carboxylic or sulfonic groups, or alternatively B and C are groups derived from carboxybetaine or sulfobetaine zwitterionic monomers;

B and C can also be chosen from cationic polymer chains comprising primary, secondary, tertiary or quaternary amine groups, wherein at least one of the amine groups bears a carboxylic or sulfonic group connected via a hydrocarbon group or alternatively B and C form part of a chain of a polymer containing an α,β-dicarboxylic ethylene unit in which one of the carboxylic groups has been made to react with a polyamine comprising at least one primary or secondary amine group.

The amphoteric fixing polymers corresponding to the definition given above that are used according to at least one embodiment are chosen from the following polymers:

(1) copolymers having acidic vinyl and basic vinyl units, such as those resulting from the copolymerization of a monomer derived from a vinyl compound bearing a carboxylic group such as, for example, acrylic acid, methacrylic acid, maleic acid, α-chloroacrylic acid, and a basic monomer derived from a substituted vinyl compound containing at least one basic atom, such as, for example, dialkylaminoalkyl methacrylate and acrylate, dialkylaminoalkylmethacrylamides and -acrylamides. Such compounds are described in U.S. Pat. No. 3,836,537.

(2) polymers comprising units derived from:
 a) at least one monomer chosen from acrylamides and methacrylamides substituted on the nitrogen atom with an alkyl group,
 b) at least one acidic comonomer containing at least one reactive carboxylic group, and
 c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate. The N-substituted acrylamides or methacrylamides that are used according to at least one embodiment of the present disclosure are compounds in which the alkyl groups contain from 2 to 12 carbon atoms, for example, N-ethylacrylamide, N-tert-butylacrylamide, N-tert-octylacrylamide, N-octylacrylamide, N-decylacrylamide, N-dodecylacrylamide and the corresponding methacrylamides.

In at least one embodiment, the acidic comonomers are chosen from acrylic acid, methacrylic acid, crotonic acid, itaconic acid, maleic acid and fumaric acid and alkyl monoesters, having 1 to 4 carbon atoms, of maleic or fumaric acids or anhydrides. According to at least one embodiment, the basic comonomers are chosen from aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer, such as the products sold under the name Amphomer® or Lovocryl® 47 by the company National Starch, are used according to at least one embodiment.

(3) crosslinked and acylated polyamino amides partially or totally derived from polyamino amides of general formula:

$$-[CO-R_{10}-CO-Z]- \quad (XIX)$$

wherein $R_{10}$ is chosen from divalent groups derived from a saturated dicarboxylic acid, mono- and dicarboxylic aliphatic acids containing an ethylenic double bond, esters of a lower alkanol, having 1 to 6 carbon atoms, of these acids, and groups derived from the addition of any one of said acids to a bis(primary) or bis(secondary) amine, and Z is chosen from groups derived from a bis(primary), mono- and bis(secondary) polyalkylene-polyamine and, in at least one embodiment, is chosen from:

a) in an amount ranging from 60 to 100 mol %, the group:

$$-NH-[(CH_2)_x-NH-]_p \quad (XX)$$

wherein x=2 and p=2 or 3, or alternatively x=3 and p=2 this group being derived from diethylenetriamine, from triethylenetetraamine or from dipropylenetriamine;

b) in an amount ranging from 0 to 40 mol %, the group (XX) above wherein x=2 and p=1 and which is derived from ethylenediamine, or the group derived from piperazine:

$$-N\underset{\phantom{a}}{\overset{\phantom{a}}{\bigcirc}}N-$$

c) in an amount ranging from 0 to 20 mol %, the —NH (CH$_2$)$_6$—NH— group being derived from hexamethylenediamine, these polyamino amides being crosslinked by addition reaction of a difunctional crosslinking agent chosen from epihalohydrins, diepoxides, dianhydrides and bis-unsaturated derivatives, using from 0.025 to 0.35 mol of crosslinking agent per amine group of the polyamino amide and acylated by the action of acrylic acid, chloroacetic acid or an alkane sultone, or salts thereof.

In at least one embodiment, the saturated carboxylic acids are chosen from acids having 6 to 10 carbon atoms, such as adipic acid, 2,2,4-trimethyladipic acid and 2,4,4-trimethyladipic acid, terephthalic acid, acids containing an ethylenic double bond such as, for example, acrylic acid, methacrylic acid and itaconic acid.

In at least one embodiment, the alkane sultones used in the acylation are propane sultone or butane sultone, the salts of the acylating agents are the sodium or potassium salts.

(4) polymers comprising zwitterionic units of formula:

$$R_{11}-[\underset{R_{13}}{\overset{R_{12}}{C}}]_y-\underset{R_{15}}{\overset{R_{14}}{N^+}}-(CH_2)_z-\overset{O}{\underset{\phantom{a}}{C}}-O^-$$

wherein $R_{11}$ is chosen from polymerizable unsaturated groups such as an acrylate, methacrylate, acrylamide or methacrylamide group, y and z are integers ranging from 1 to 3, $R_{12}$ and $R_{13}$ are chosen from hydrogen atoms, methyl, ethyl and propyl groups, $R_{14}$ and $R_{15}$ are chosen from hydrogen atoms and alkyl groups such that the sum of the carbon atoms in $R_{14}$ and $R_{15}$ does not exceed 10.

The polymers comprising such units can also comprise units derived from nonzwitterionic monomers such as dimethyl- or diethylaminoethyl acrylate or methacrylate, or alkyl acrylates or methacrylates, acrylamides or methacrylamides or vinyl acetate.

By way of example, non-limiting mention may be made of the copolymers of methyl methacrylate/methyl dimethylcarboxymethylammonioethyl methacrylate such as the product sold under the name Diaformer Z301 by the company Sandoz.

(5) polymers derived from chitosan comprising monomer units corresponding to the following formulae:

(D)

[chitosan unit D structure with CH$_2$OH and NHCOCH$_3$]

(E)

[chitosan unit E structure with CH$_2$OH and NH$_2$]

(F)

[chitosan unit F structure with CH$_2$OH and NH—C(=O)—R$_{16}$—COOH]

the unit (D) being present in an amount ranging from 0 to 30%, the unit (E) being present in an amount ranging from 5 to 50% and the unit (F) being present in an amount ranging from 30% to 90%, it being understood that, in this unit (F), $R_{16}$ is a group of formula:

$$R_{17}-\underset{\phantom{a}}{\overset{R_{18}}{C}}-(O)_q-\overset{R_{19}}{\underset{\phantom{a}}{C}}$$

wherein, if q=0, $R_{17}$, $R_{18}$ and $R_{19}$, which may be identical or different, are chosen from hydrogen atoms, methyl groups, hydroxyl groups, acetoxy groups, amino residues, monoalkylamine residues and dialkylamine residues that are optionally interrupted by at least one nitrogen atom and/or optionally substituted with at least one group chosen from amine, hydroxyl, carboxyl, alkylthio and sulfonic group, an alkylthio residue wherein the alkyl group bears an amino residue, at least one of the groups $R_{17}$, $R_{18}$ and $R_{19}$ being, in this case, a hydrogen atom;

or, if q=1, $R_{17}$, $R_{18}$ and $R_{19}$ each represent a hydrogen atom, as well as the salts formed by these compounds with bases or acids.

(6) polymers of formula (XXII), which are described, for example, in French Patent No. 1 400 366:

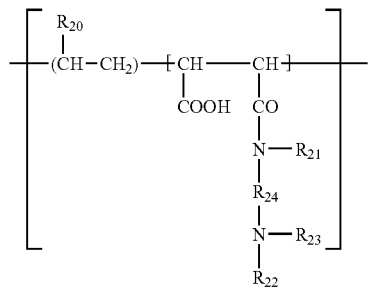

(XXII)

wherein $R_{20}$ is chosen from a hydrogen atom, $CH_3O$, $CH_3CH_2O$ and a phenyl group, $R_{21}$ is chosen from a hydrogen atom and lower alkyl groups such as methyl or ethyl, $R_{22}$ is chosen from a hydrogen atom and $C_{1-6}$ lower alkyl groups such as methyl or ethyl, $R_{23}$ is chosen from $C_{1-6}$ lower alkyl groups such as methyl or ethyl and groups of formula: —$R_{24}$—$N(R_{22})_2$, wherein $R_{24}$ is chosen from —$CH_2$—$CH_2$—, —$CH_2$—$CH_2$—$CH_2$— and —$CH_2$—$CH(CH_3)$— groups, $R_{22}$ having the meaning defined above, (7) polymers derived from the N-carboxyalkylation of chitosan, such as N-carboxymethylchitosan or N-carboxybutylchitosan sold under the name Evalsan by the company Jan Dekker.

(8) amphoteric polymers of the type -D-X-D-X- chosen from:
 a) polymers obtained by the action of chloroacetic acid or sodium chloroacetate on compounds comprising at least one unit of formula (XXIII):

-D-X-D-X-D- (XXIII)

wherein D is a group

and X is the symbol E or E', wherein E or E', which may be identical or different, are chosen from divalent groups that are alkylene groups with a straight or branched chain containing up to 7 carbon atoms in the main chain, which is unsubstituted or substituted with hydroxyl groups and which can comprise, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups.

b) polymers of formula (XXIV'):

-D-X-D-X- (XXIV')

wherein D is a group

and X is the symbol E or E' and at least once E'; E having the meaning given above and E' is chosen from divalent groups that are alkylene groups with a straight or branched chain having up to 7 carbon atoms in the main chain, which is unsubstituted or substituted with at least one hydroxyl group and containing at least one nitrogen atom, the nitrogen atom being substituted with an alkyl chain that is optionally interrupted by an oxygen atom and necessarily comprising at least one carboxyl functional group or at least one hydroxyl functional group and betainized by reaction with chloroacetic acid or sodium chloroacetate.

(9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkylaminoalkanol. These copolymers can also comprise other vinyl comonomers such as vinylcaprolactam.

Among the amphoteric fixing polymers described above, those that are used according to at least one embodiment of the present disclosure are those of family (3), such as the copolymers whose CTFA name is octylacrylamide/acrylates/butylaminoethyl methacrylate copolymer, such as the products sold under the names Amphomer®, Amphomer® LV 71 or Lovocryl® 47 by the company National Starch and those of family (4) such as the copolymers of methyl methacrylate/methyl dimethylcarboxymethylammonioethyl methacrylate, sold, for example, under the name Diaformer® Z301 by the company Sandoz.

The nonionic fixing polymers that may be used according to at least one embodiment of the present disclosure are chosen., for example, from:
 polyalkyloxazolines;
 vinyl acetate homopolymers;
 vinyl acetate copolymers, for instance copolymers of vinyl acetate and of acrylic ester; copolymers of vinyl acetate and of ethylene; copolymers of vinyl acetate and of maleic ester, for example of dibutyl maleate;
 homopolymers and copolymers of acrylic esters, for instance copolymers of alkyl acrylates and of alkyl methacrylates, such as the products sold by the company Rohm & Haas under the names Primal® AC-261 K and Eudragit® NE 30 D, by the company BASF under the name 8845, or by the company Hoechst under the name Appretan® N9212;
 copolymers of acrylonitrile and of a nonionic monomer chosen, for example, from butadiene and alkyl (meth) acrylates; non-limiting mention may be made of the products sold under the name CJ 0601 B by the company Rohm & Haas;
 styrene homopolymers;
 styrene copolymers, for instance copolymers of styrene and of an alkyl(meth)acrylate, such as the products Mowilith® LDM 6911, Mowilith® DM 611 and Mowilith® LDM 6070 sold by the company Hoechst, and the products Rhodopas® SD 215 and Rhodopas® DS 910 sold by the company Rhodia Chimie; copolymers of styrene, of alkyl methacrylate and of alkyl acrylate;

copolymers of styrene and of butadiene; or copolymers of styrene, of butadiene and of vinylpyridine;

polyamides;

vinyllactam homopolymers other than vinylpyrrolidone homopolymers, such as the polyvinylcaprolactam sold under the name Luviskol® Plus by the company BASF; and vinyllactam copolymers such as a poly(vinylpyrrolidone/vinyllactam) copolymer sold under the trade name Luvitec® VPC 55K65W by the company BASF, poly(vinylpyrrolidone/vinyl acetate) copolymers, such as those sold under the name PVPVA® S630L by the company ISP, Luviskol® VA 73, VA 64, VA 55, VA 37 and VA 28 by the company BASF; and poly(vinylpyrrolidone/vinyl acetate/vinyl propionate)terpolymers, for instance the product sold under the name Luviskol® VAP 343 by the company BASF.

In at least one embodiment, the alkyl groups of the nonionic polymers mentioned above contain from 1 to 6 carbon atoms.

Functionalized or non-functionalized, silicone or non-silicone, cationic, nonionic, anionic or amphoteric polyurethanes or mixtures thereof may also be used as fixing polymers.

The polyurethanes used in at least one embodiment of the present disclosure are those disclosed in European Patent Nos. EP 0 751 162, EP 0 637 600, and EP 0 648 485, and French Patent No. FR 2 743 297, and European Patent No. EP 0 656 021 and International Patent Application No. WO 94/03510 from the company BASF, and European Patent No. EP 0 619 111 from the company National Starch.

Among polyurethanes that may be used according to at least one embodiment of the present disclosure, non-limiting mention may be made of the products sold under the names Luviset Pur® and Luviset® Si-Pur by the company BASF.

The at least one additional fixing polymer can be present in the cosmetic composition according to at least one embodiment of the present disclosure in an amount ranging from 0.01% to 20% by weight, such as from 0.05% to 15% by weight or from 0.1% to 10% by weight, relative to the total weight of the cosmetic composition.

The cosmetic composition according to the present disclosure may also comprise at least one "rheology modifier."

The at least one rheology modifier may be chosen from fatty acid amides (coconut diethanolamide or monoethanolamide, or oxyethylenated monoethanolamide of carboxylic acid alkyl ether), cellulose-based thickeners (hydroxyethylcellulose, hydroxypropylcellulose or carboxymethylcellulose), guar gum and its derivatives (hydroxypropyl guar), gums of microbial origin (xanthan gum, scieroglucan gum), crosslinked homopolymers of acrylic acid or of acrylamidopropanesulfonic acid, and associative polymers such as those described below other than the polymers of the present disclosure.

The associative polymers that may be used in the cosmetic composition according to at least one embodiment of the present disclosure are water-soluble polymers capable, in an aqueous medium, of reversibly combining with each other or with other molecules. Their chemical structure comprises hydrophilic zones and hydrophobic zones characterized by at least one fatty chain.

The associative polymers that may be used according to the present disclosure may be of anionic, cationic, amphoteric or nonionic type. In at least one embodiment of the present disclosure, the at least one associative polymer is nonionic.

Among the associative polymers of anionic type that may be used according to at least one embodiment, non-limiting mention may be made of:

(I) those comprising at least one hydrophilic unit and at least one fatty-chain allyl ether unit, such as those whose hydrophilic unit comprises an ethylenic unsaturated anionic monomer, such as of a vinylcarboxylic acid and, for example, of an acrylic acid or a methacrylic acid or mixtures thereof, the fatty-chain allyl ether unit of which is chosen from those of formula (XXV):

$$CH_2=CR'CH_2OB_nR \quad (XXV)$$

wherein R' is chosen from H and $CH_3$, B is an ethyleneoxy radical, n is an integer ranging from 0 to 100, R is a hydrocarbon-based radical chosen from alkyl, arylalkyl, aryl, alkylaryl and cycloalkyl radicals, containing from 8 to 30 carbon atoms, such as from 10 to 24 carbon atoms or from 12 to 18 carbon atoms. A unit of formula (XXV) that is used according to at least one embodiment is a unit wherein R' is H, n is equal to 10 and R is a stearyl ($C_{18}$) radical.

Anionic associative polymers of this type are described and prepared, according to an emulsion polymerization process, in European Patent No. EP-0 216 479.

Among these anionic associative polymers that are used according to at least one embodiment of the present disclosure are polymers formed from 20% to 60% by weight of acrylic acid and/or of methacrylic acid, from 5% to 60% by weight of lower alkyl (meth)acrylates, from 2% to 50% by weight of fatty-chain allyl ether of formula (XXV), and from 0% to 1% by weight of a crosslinking agent which is a well-known copolymerizable unsaturated polyethylenic monomer, for instance diallyl phthalate, allyl(meth)acrylate, divinylbenzene, (poly)ethylene glycol dimethacrylate or methylenebisacrylamide. Among the latter polymers, those used according to at least one further embodiment are crosslinked terpolymers of methacrylic acid, of ethyl acrylate and of polyethylene glycol (10 EO) stearyl alcohol ether (Steareth-10), including those sold by the company Allied Colloids under the names Salcare SC 80® and Salcare SC 90®, which are aqueous 30% emulsions of a crosslinked terpolymer of methacrylic acid, of ethyl acrylate and of steareth-10 allyl ether (40/50/10).

(II) those comprising at least one hydrophilic unit of unsaturated olefinic carboxylic acid type, and at least one hydrophobic unit of ($C_{10}$-$C_{30}$)alkyl ester of unsaturated carboxylic acid type.

In at least one embodiment, these polymers are chosen from those in which the hydrophilic unit of unsaturated olefinic carboxylic acid type is a monomer of formula (XXVI):

$$CH_2=\underset{R_1}{\underset{|}{C}}-\underset{O}{\underset{\|}{C}}-OH \quad (XXVI)$$

wherein $R_1$ is chosen from H, $CH_3$, and $C_2H_5$, that is to say acrylic acid, methacrylic acid or ethacrylic acid units, and wherein the hydrophobic unit of ($C_{10}$-$C_{30}$)alkyl ester of unsaturated carboxylic acid type is a monomer of formula (XXVII):

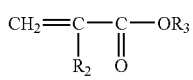 (XXVII)

wherein $R_2$ is chosen from H, $CH_3$ and $C_2H_5$ (that is to say acrylate, methacrylate or ethacrylate units), for example, H (acrylate units) or $CH_3$ (methacrylate units), $R_3$ is chosen from $C_{10}$-$C_{30}$ alkyl radicals, such as $C_{12}$-$C_{22}$ alkyl radicals.

($C_{10}$-$C_{30}$) alkyl esters of unsaturated carboxylic acids according to at least one embodiment of the present disclosure include, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to U.S. Pat. Nos. 3,915,921 and 4,509,949.

Among the anionic associative polymers of this type that are used in at least one embodiment of the present disclosure, are polymers formed from a monomer mixture
(i) essentially acrylic acid,
(ii) an ester of formula (XXVII) described above in which $R_2$ is H or $CH_3$, $R_3$ is chosen from alkyl radicals containing from 12 to 22 carbon atoms, and
(iii) a crosslinking agent, which is a well-known copolymerizable unsaturated polyethylenic monomer, for instance diallyl phthalate, allyl(meth)acrylate, divinylbenzene, (poly)ethylene glycol dimethacrylate and methylenebisacrylamide.

Among anionic associative polymers of this type that will be used according to at least one embodiment are those comprising from 95% to 60% by weight of acrylic acid (hydrophilic unit), 4% to 40% by weight of $C_{10}$-$C_{30}$-alkyl acrylate (hydrophobic unit) and 0% to 6% by weight of crosslinking polymerizable monomer, or alternatively those comprising from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described above.

Among the above polymers, those used according to at least one further embodiment of the present disclosure are the products sold by the company Goodrich under the trade names Pemulen TR1®, Pemulen TR2® and Carbopol 1382®, such as, for example, Pemulen TR1®, and the product sold by the company SEPPIC under the name Coatex Sx®.

(III) maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608® by the company Newphase Technologies.

(IV) acrylic terpolymers comprising:
(a) 20% to 70% by weight of a carboxylic acid containing α,β-monoethylenic unsaturation,
(b) 20% to 80% by weight of a non-surfactant monomer containing α,β-monoethylenic unsaturation other than (a), and
(c) 0.5% to 60% by weight of a nonionic monourethane which is the product of reaction of a monohydric surfactant with a monoisocyanate containing monoethylenic unsaturation,
such as those described in European Patent Application No. EP-A-0 173 109, such as, for example, the terpolymer described in Example 3, namely a methacrylic acid/methyl acrylate/behenyl alcohol dimethyl-meta-isopropenylbenzyl-isocyanate ethoxylated (40 EO) terpolymer, as an aqueous 25% dispersion.

(V) copolymers comprising among their monomers a carboxylic acid containing α,β-monoethylenic unsaturation and an ester of a carboxylic acid containing α,β-monoethylenic unsaturation and of an oxyalkylenated fatty alcohol.

In at least one embodiment, these compounds also comprise as monomers an ester of a carboxylic acid containing α,β-monoethylenic unsaturation and of a $C_1$-$C_4$ alcohol.

An example of a compound of this type that may be mentioned is Aculyn 22® sold by the company Rohm & Haas, which is a methacrylic acid/ethyl acrylate/stearyl methacrylate oxyalkylenated terpolymer.

Among the associative polymers of cationic type that may be used, non-limiting mention may be made of:
(I) cationic associative polyurethanes, the family of which has been described in French Patent Application No. 00/09609; and which may be represented by the general formula (XXVIII):

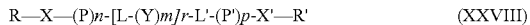 (XXVIII)

wherein:
R and R', which may be identical or different, are chosen from hydrophobic groups and hydrogen atoms;
X and X', which may be identical or different, are chosen from groups comprising an amine functional group optionally bearing a hydrophobic group, or alternatively a group L";
L, L' and L", which may be identical or different, are chosen from groups derived from a diisocyanate;
P and P'', which may be identical or different, are chosen from groups comprising an amine functional group optionally bearing a hydrophobic group;
Y is chosen from hydrophilic groups;
r is an integer ranging from 1 to 100, such as from 1 to 50 or from 1 to 25;
n, m and p each range, independently of each other, from 0 to 1000;
wherein the molecule containing at least one protonated or quaternized amine functional group and at least one hydrophobic group.

In at least one embodiment of these polyurethanes, the only hydrophobic groups are the groups R and R' at the chain ends.

According to at least one embodiment, the family of cationic associative polyurethanes used is the one of formula (XXVIII) described above and in which:
R and R' both independently are chosen from hydrophobic groups,
X and X' each are chosen from groups L",
n and p range from 1 to 1000, and
L, L', L", P, P', Y and m have the meaning given above.

In at least one other embodiment, the family of cationic associative polyurethanes used is the one corresponding to formula (XXVIII) above wherein:
R and R' both independently are chosen from hydrophobic groups, X and X' each are chosen from groups L", n and p are 0, and L, L', L", Y and m have the meaning given above.

The fact that n and p are 0 means that these polymers do not comprise units derived from a monomer containing an amine functional group, incorporated into the polymer during the polycondensation. The protonated amine functional groups of these polyurethanes result from the hydrolysis of excess isocyanate functional groups, at the chain end, followed by alkylation of the primary amine functional groups formed with alkylating agents containing a hydrophobic group, i.e., compounds of the type RQ or R'Q, wherein R and R' are as defined above and Q is a leaving group such as a halide, a sulfate, etc.

Another family of cationic associative polyurethanes used in at least one embodiment is that of formula (XXVIII) above wherein:

R and R' both independently are chosen from hydrophobic groups,

X and X' both independently are chosen from groups comprising a quaternary amine, n and p are zero, and L, L', Y and m have the meaning given above.

In at least one embodiment, the number-average molecular mass of the cationic associative polyurethanes ranges from 400 to 500,000, such as from 1000 to 400,000 or from 1000 to 300,000.

In the context of the present disclosure, the expression "hydrophobic group" means a radical or polymer containing a saturated or unsaturated, linear or branched hydrocarbon-based chain, which may contain at least one hetero atom such as P, O, N or S, or a radical containing a perfluoro or silicone chain. When the hydrophobic group is a hydrocarbon-based radical, it comprises at least 10 carbon atoms, such as from 10 to 30 carbon atoms, from 12 to 30 carbon atoms or from 18 to 30 carbon atoms.

In at least one embodiment, the hydrocarbon-based group is derived from a monofunctional compound.

By way of non-limiting example, the hydrophobic group may be derived from a fatty alcohol such as stearyl alcohol, dodecyl alcohol or decyl alcohol. It may also denote a hydrocarbon-based polymer such as, for example, polybutadiene.

When X and/or X' is chosen from groups comprising a tertiary or quaternary amine, X and/or X' may be chosen from one of the following formulae:

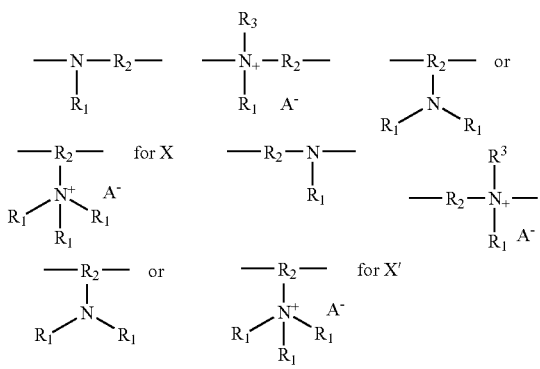

wherein:

$R_2$ is chosen from linear and branched alkylene radicals containing from 1 to 20 carbon atoms, optionally comprising a saturated or unsaturated ring, and arylene radicals, wherein at least one of the carbon atoms is optionally replaced with a hetero atom chosen from N, S, O and P;

$R_1$ and $R_3$, which may be identical or different, are chosen from linear and branched $C_1$-$C_{30}$ alkyl or alkenyl radicals and aryl radicals, wherein at least one of the carbon atoms is optionally replaced with a hetero atom chosen from N, S, O and P;

$A^-$ is a physiologically acceptable counterion.

The groups L, L' and L" are chosen from groups of formula:

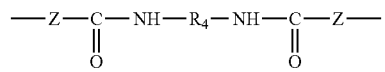

wherein:

Z is chosen from —O—, —S— and —NH—; and $R_4$ is chosen from linear and branched alkylene radicals containing from 1 to 20 carbon atoms, optionally comprising a saturated or unsaturated ring, and arylene radicals, wherein at least one of the carbon atoms is optionally replaced with a hetero atom chosen from N, S, O and P.

The groups P and P' comprising an amine functional group may be chosen from at least one of the following formulae:

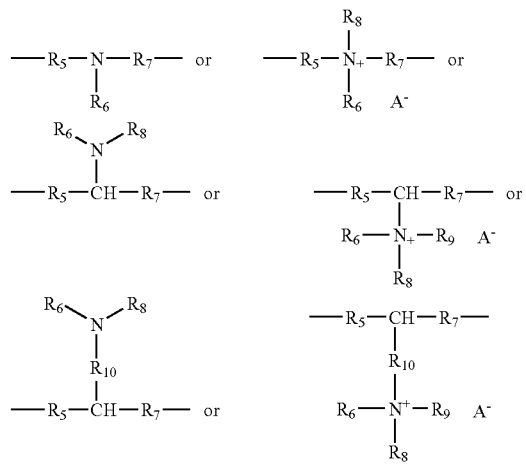

wherein:

$R_5$ and $R_7$, which may be identical or different, are chosen from linear and branched alkylene radicals containing from 1 to 20 carbon atoms, optionally comprising a saturated or unsaturated ring, and arylene radicals, wherein at least one of the carbon atoms is optionally replaced with a hetero atom chosen from N, S, O and P;

$R_6$, $R_8$ and $R_9$ which may be identical or different, are chosen from linear and branched $C_1$-$C_{30}$ alkyl or alkenyl radicals and aryl radicals, wherein at least one of the carbon atoms is optionally replaced with a hetero atom chosen from N, S, O and P;

$R_{10}$ is chosen from linear and branched, optionally unsaturated alkylene groups optionally containing at least one hetero atom chosen from N, O, S and P; and $A^-$ is a physiologically acceptable counterion.

As regards the meaning of Y, the term "hydrophilic group" means a polymeric or non-polymeric water-soluble group.

By way of example, when Y is not a polymer, non-limiting mention may be made of ethylene glycol, diethylene glycol and propylene glycol.

When Y is a hydrophilic polymer, in accordance with at least one embodiment, non-limiting mention may be made, for example, of polyethers, sulfonated polyesters, sulfonated polyamides or a mixture of these polymers. In at least one embodiment, the hydrophilic compound is a polyether, such as a poly(ethylene oxide) or poly(propylene oxide).

The cationic associative polyurethanes of formula (XXVIII) that may be used according to the present disclosure are formed from diisocyanates and from various compounds with functional groups containing a labile hydrogen. The functional groups containing a labile hydrogen may be alcohol, primary or secondary amine or thiol functional groups, giving, after reaction with the diisocyanate functional groups, polyurethanes, polyureas and polythioureas, respectively. The expression "polyurethanes which can be used according to the present disclosure" encompasses these three types of polymer, namely polyurethanes per se, polyureas and polythioureas, and also copolymers thereof.

A first type of compound involved in the preparation of the polyurethane of formula (XXVIII) is a compound comprising at least one unit containing an amine functional group. This compound may be multifunctional, but in at least one embodiment, the compound is difunctional. That is to say that, according to at least one embodiment, this compound comprises two labile hydrogen atoms borne, for example, by a hydroxyl, primary amine, secondary amine or thiol functional group. A mixture of multifunctional and difunctional compounds in which the percentage of multifunctional compounds is low may also be used.

As mentioned above, this compound may comprise more than one unit containing an amine functional group. In this case, it is a polymer bearing a repetition of the unit containing an amine functional group.

Compounds of this type may be chosen from those of formulae:

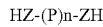
HZ-(P)n-ZH and

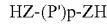
HZ-(P')p-ZH wherein Z, P, P', n and p are as defined above.

Examples of compounds containing an amine functional group that may be used according to at least one embodiment, non-limiting mention may be made of N-methyldiethanolamine, N-tert-butyldiethanolamine and N-sulfoethyldiethanolamine.

The second compound involved in the preparation of the polyurethane of formula (XXVIII) is a diisocyanate of formula:

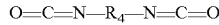
O=C=N—R$_4$—N=C=O wherein R$_4$ is as defined above.

By way of example, non-limiting mention may be made of methylenediphenyl diisocyanate, methylenecyclohexane diisocyanate, isophorone diisocyanate, tolylene diisocyanate, naphthalene diisocyanate, butane diisocyanate and hexane diisocyanate.

A third compound involved in the preparation of the polyurethane of formula (XXVIII) is a hydrophobic compound intended to form the terminal hydrophobic groups of the polymer of formula (XXVIII).

This compound comprises a hydrophobic group and a functional group containing a labile hydrogen, for example a hydroxyl, primary or secondary amine, or thiol functional group.

By way of non-limiting example, this compound may be a fatty alcohol such as, for example, stearyl alcohol, dodecyl alcohol or decyl alcohol. When this compound comprises a polymeric chain, it may be, for example, α-hydroxylated hydrogenated polybutadiene.

The hydrophobic group of the polyurethane of formula (XXVIII) may also result from the quaternization reaction of the tertiary amine of the compound comprising at least one tertiary amine unit. Thus, the hydrophobic group can be introduced via the quaternizing agent. This quaternizing agent can be a compound of the type RQ or R'Q, wherein R and R' are as defined above and Q is a leaving group such as a halide, a sulfate, etc.

The cationic associative polyurethane may also comprise a hydrophilic block. This block can be provided by a fourth type of compound involved in the preparation of the polymer. This compound may be multifunctional. In at least one embodiment, it is difunctional. It is also possible to have a mixture in which the percentage of multifunctional compound is low.

The functional groups containing a labile hydrogen include alcohol, primary or secondary amine or thiol functional groups. This compound may be a polymer terminated at the chain ends with one of these functional groups containing a labile hydrogen.

By way of example, when the multifunctional compound is not a polymer, non-limiting mention may be made of ethylene glycol, diethylene glycol and propylene glycol.

When it is a hydrophilic polymer, non-limiting mention may be made, for example, of polyethers, sulfonated polyesters and sulfonated polyamides, or a mixture of these polymers. In at least one embodiment, the hydrophilic compound is a polyether, such as a poly(ethylene oxide) or poly(propylene oxide).

The hydrophilic group termed Y in formula (XXVIII) is optional. Specifically, the units containing a quaternary amine or protonated functional groups may suffice to provide the solubility or water-dispersibility required for this type of polymer in an aqueous solution.

Although the presence of a hydrophilic group Y is optional, cationic associative polyurethanes comprising such a group are, however, used in at least one embodiment of the present disclosure.

(II) quaternized cellulose derivatives and polyacrylates containing non-cyclic amine side groups.

The quaternized cellulose derivatives can be chosen from, by way of non-limiting example:
  quaternized celluloses modified with groups comprising at least one fatty chain, such as alkyl, arylalkyl or alkylaryl groups containing at least 8 carbon atoms, or mixtures thereof.
  quaternized hydroxyethylcelluloses modified with groups comprising at least one fatty chain, such as alkyl, arylalkyl or alkylaryl groups containing at least 8 carbon atoms, or mixtures thereof.

The alkyl radicals borne by the above quaternized celluloses or hydroxyethylcelluloses may contain from 8 to 30 carbon atoms. The aryl radicals can be chosen, for example, from phenyl, benzyl, naphthyl and anthryl groups.

Non-limiting examples of quaternized alkylhydroxyethylcelluloses containing $C_8$-$C_{30}$ fatty chains that may be mentioned include the products Quatrisoft LM 200®, Quatrisoft LM-X 529-18-A®, Quatrisoft LM-X 529-18B® ($C_{12}$ alkyl) and Quatrisoft LM-X 529-8® ($C_{18}$ alkyl) sold by the company Amerchol, and the products Crodacel QM®, Crodacel QL® ($C_{12}$ alkyl) and Crodacel QS® ($C_{18}$ alkyl) sold by the company Croda.

The amphoteric associative polymers can bee chosen from those comprising at least one non-cyclic cationic unit. In at least one embodiment, the ones used are those prepared from or comprising 1 to 20 mol %, such as from 1.5 to 15 mol % or from 1.5 to 6 mol %, of fatty-chain monomer relative to the total number of moles of monomers.

The amphoteric associative polymers that are used according to at least one embodiment of the present disclosure comprise or are prepared by copolymerizing:
  1) at least one monomer chosen from those of formulae (XXIX) and (XXX):

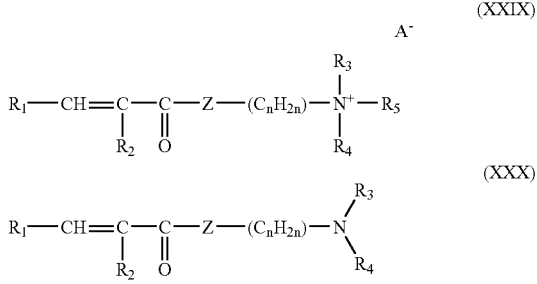

(XXIX)

(XXX)

wherein $R_1$ and $R_2$, which may be identical or different, are chosen from hydrogen atoms and methyl radicals, $R_3$, $R_4$ and $R_5$, which may be identical or different, are chosen from linear and branched alkyl radicals containing from 1 to 30 carbon atoms, Z is chosen from an NH group and an oxygen atom, n is an integer ranging from 2 to 5, $A^-$ is an anion derived from an organic or mineral acid, such as a methosulfate anion or a halide such as chloride or bromide;

2) at least one monomer of formula (XXXI)

$$R_6-CH=CR_7-COOH \qquad (XXXI)$$

wherein $R_6$ and $R_7$, which may be identical or different, are chosen from hydrogen atoms and methyl radicals; and 3) at least one monomer of formula (XXXIII):

$$R_6-CH=CR_7-COXR_8 \qquad (XXXIII)$$

wherein $R_6$ and $R_7$, which may be identical or different, are chosen from hydrogen atoms and methyl radicals, X is an oxygen or nitrogen atom and $R_8$ is chosen from linear and branched alkyl radicals containing from 1 to 30 carbon atoms; wherein at least one of the monomers of formula (XXIX), (XXX) or (XXXIII) comprises at least one fatty chain.

In at least one embodiment, the monomers of formulae (XXIX) and (XXX) of the present disclosure are chosen from:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, and dimethylaminopropylmethacrylamide, dimethylaminopropylacrylamide, these monomers optionally being quaternized, for example with a $C_1$-$C_4$ alkyl halide or a $C_1$-$C_4$ dialkyl sulfate.

In at least one embodiment, the monomer of formula (XXIX) is chosen from acrylamidopropyltrimethylammonium chloride and methacrylamidopropyltrimethylammonium chloride.

According to at least one embodiment, the monomers of formula (XXXI) of the present disclosure are chosen from acrylic acid, methacrylic acid, crotonic acid and 2-methylcrotonic acid. For example, the monomer of formula (XXXI) can be acrylic acid.

The monomers of formula (XXXIII), according to at least one embodiment, are chosen from $C_{12}$-$C_{22}$ alkyl acrylates or methacrylates, such as $C_{16}$-$C_{18}$ alkyl acrylates or methacrylates.

The monomers constituting the fatty-chain amphoteric polymers according to at least one embodiment of the present disclosure are already neutralized and/or quaternized.

The ratio of the number of cationic charges/anionic charges is equal to about 1 in at least one embodiment.

The amphoteric associative polymers according to at least one embodiment of the present disclosure comprise from 1 mol % to 10 mol % of the monomer comprising a fatty chain (monomer of formulae (XXIX), (XXX) or (XXXIII)), such as from 1.5 mol % to 6 mol %.

The weight-average molecular weights of the amphoteric associative polymers according to at least one embodiment of the present disclosure may range from 500 to 50,000,000, such as from 10,000 to 5,000,000.

The amphoteric associative polymers according to the present disclosure may also contain other monomers such as nonionic monomers, for example, $C_1$-$C_4$ alkyl acrylates or methacrylates.

Amphoteric associative polymers according to the present disclosure are described and prepared, for example, in International Patent Application No. WO 98/44012.

Among the amphoteric associative polymers according to at least one embodiment of the present disclosure, non-limiting mention may be made of acrylic acid/(meth)acrylamidopropyltrimethylammonium chloride/stearyl methacrylate terpolymers.

The associative polymers of nonionic type that may be used according to the present disclosure can be chosen from:

(1) celluloses modified with groups comprising at least one fatty chain; non-limiting examples that may be mentioned include:

hydroxyethylcelluloses modified with groups comprising at least one fatty chain, such as alkyl, arylalkyl or alkylaryl groups, or mixtures thereof, and in which the alkyl groups are, for example, $C_8$-$C_{22}$, for instance the product Natrosol Plus Grade 330 CS® ($C_{16}$ alkyls) sold by the company Aqualon, or the product Bermocoll EHM 100® sold by the company Berol Nobel, those modified with alkylphenyl polyalkylene glycol ether groups, such as the product Amercell Polymer HM-1500® (nonylphenyl polyethylene glycol (15) ether) sold by the company Amerchol.

(2) hydroxypropyl guars modified with groups comprising at least one fatty chain, such as the product Esaflor HM 22® ($C_{22}$ alkyl chain) sold by the company Lamberti, and the products RE210-18® ($C_{14}$ alkyl chain) and RE205-1® ($C_{20}$ alkyl chain) sold by the company Rhône-Poulenc.

(3) copolymers of vinylpyrrolidone and of fatty-chain hydrophobic monomers; non-limiting examples that may be mentioned include:

the products Antaron V216® or Ganex V216® (vinylpyrrolidone/hexadecene copolymer) sold by the company I.S.P.

the products Antaron V220® or Ganex V220® (vinylpyrrolidone/eicosene copolymer) sold by the company I.S.P.

(4) copolymers of $C_1$-$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208®.

(5) copolymers of hydrophilic methacrylates or acrylates and of hydrophobic monomers comprising at least one fatty chain, such as, for example, the polyethylene glycol methacrylate/lauryl methacrylate copolymer.

(6) polyurethane polyethers comprising in their chain both hydrophilic blocks usually of polyoxyethylenated nature, and hydrophobic blocks which may be aliphatic sequences alone and/or cycloaliphatic and/or aromatic sequences.

(7) polymers with an aminoplast ether skeleton containing at least one fatty chain, such as the Pure Thix® compounds sold by the company Sud-Chemie.

In at least one embodiment, the polyurethane polyethers comprise at least two hydrocarbon-based lipophilic chains containing from 6 to 30 carbon atoms, separated by a hydrophilic block, the hydrocarbon-based chains optionally being pendent chains, or chains at the end of the hydrophilic block. In at least one further embodiment, it is possible for at least one pendent chain to be included. In addition, the polymer may comprise a hydrocarbon-based chain at one end or at both ends of a hydrophilic block.

The polyurethane polyethers may be multiblock, such as in triblock form. Hydrophobic blocks may be at each end of the chain (for example: triblock copolymer with a hydrophilic central block) or distributed both at the ends and in the chain (for example: multiblock copolymer). These same polymers may also be graft polymers or starburst polymers.

The nonionic fatty-chain polyurethane polyethers may be triblock copolymers in which the hydrophilic block is a polyoxyethylenated chain comprising from 50 to 1000 oxyethylene groups. The nonionic polyurethane polyethers comprise a urethane linkage between the hydrophilic blocks, whence arises the name.

By extension, also included among the nonionic fatty-chain polyurethane polyethers are those in which the hydrophilic blocks are linked to the lipophilic blocks via other chemical bonds.

As non-limiting examples of nonionic fatty-chain polyurethane polyethers that may be used according to the present disclosure, it is also possible to use Rheolate 205® containing a urea function, sold by the company Rheox, or Rheolate® 208, 204 or 212, and also Acrysol RM 184®.

Non-limiting mention may also be made of the product Elfacos T210® containing a $C_{12-14}$ alkyl chain, and the product Elfacos T212® containing a $C_{18}$ alkyl chain, from Akzo.

The product DW 1206B® from Rohm & Haas containing a $C_{20}$ alkyl chain and a urethane linkage, sold at a solids content of 20% in water, may also be used.

It is also possible to use solutions or dispersions of these polymers, such as in water or in aqueous-alcoholic medium. Non-limiting examples of such polymers that may be mentioned are Rheolate® 255, Rheolate® 278 and Rheolate® 244 sold by the company Rheox. The products DW 1206F and DW 1206J sold by the company Rohm & Haas may also be used.

The polyurethane polyethers that may be used according to at least one embodiment of the present disclosure are those described, for example, in the article by G. Fonnum, J. Bakke and Fk. Hansen—Colloid Polym. Sci., 271, 380-389 (1993).

In at least one embodiment, a polyurethane polyether is used that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold, for example, by the company Rohm & Haas under the names Aculyn 44® and Aculyn 46®: Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexylisocyanate) (SMDI), at 35% by weight in a mixture of propylene glycol (39%) and water (26%).

The at least one rheology modifier nmay be present in the cosmetic composition according to the present disclosure in an amount ranging from 0.01% to 20% by weight, such as in an amount ranging from 0.05% to 10% by weight or from 0.1% to 5% by weight, relative to the total weight of the composition.

The cosmetic composition according to the disclosure may also comprise at least one cosmetic adjuvants chosen from cationic, anionic, amphoteric and nonionic surfactants; silicones other than those of the present disclosure; conditioning agents of ester type; antifoams; moisturizers; emollients; plasticizers; water-soluble and liposoluble, silicone-based and non-silicone-based sunscreens; permanent and temporary dyes; fragrances; peptizers; preserving agents; ceramides; pseudoceramides; vitamins and provitamins, including panthenol; proteins; sequestrants; solubilizers; basifying agents; anticorrosion agents; fatty substances such as plant, animal, mineral and synthetic oils; reducing agents and antioxidants; and oxidizing agents.

A person skilled in the art will take care to select the optional adjuvants and the amount thereof such that they do not harm the beneficial properties of the compositions of the present disclosure.

In at least one embodiment, the at least one cosmetic adjuvant is present in an amount ranging from 0.001% to 50% by weight relative to the total weight of the composition.

In the context of the present disclosure, the term "cosmetically acceptable medium" means a medium that is compatible with keratin materials, including the hair.

The cosmetically acceptable medium may be an alcoholic, aqueous or aqueous-alcoholic medium. Thus, in at least one embodiment, the medium may consist of water, or consist of alcohol, or comprise water and at least one cosmetically acceptable solvent, such as $C_1$-$C_4$ lower alcohols, polyols, polyol monoethers, and mixtures thereof. In at least one embodiment, the alcohol is ethanol.

The cosmetic compositions in accordance with the present disclosure may be in the form of a cream, a mousse, a lotion, a spray, a gel or a hair conditioner.

The cosmetic compositions in accordance with the present disclosure may also be packaged in a pump-dispenser bottle or in an aerosol device that is common in cosmetics.

When packed in an aerosol device, the cosmetic compositions as disclosed herein further comprise at least one propellant. The at least one propellant used in the aerosol systems according to at least one embodiment of the disclosure may be chosen from air, nitrogen, carbon dioxide, dimethyl ether, $C_3$ to $C_5$ alkanes and 1,1-difluoroethane.

The present disclosure also relates to an aerosol device comprising the compositions described above with an appropriate device for distributing this composition.

The present disclosure also relates to a cosmetic process for treating, for example styling, the hair, comprising applying an effective amount of a composition described above to wet or dry hair, and optionally rinsing the hair after an optional period of leave-in time or after optional drying.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the invention are approximations, the numerical values set forth in the specific examples are reported as precisely as possible. Any numerical value, however, inherently contains certain errors necessarily resulting from the standard deviation found in its respective testing measurement.

The example that follows is given as a non-limiting illustration of the present disclosure.

EXAMPLE

Compositions (A) to (D) in accordance with the disclosure were prepared from the following compounds:

| Composition A | |
|---|---|
| Styleze W20 [1] | 1% |
| Cetyl alcohol | 3% |
| Amodimethicone (DC 939) | 1.5% |
| Cetyltrimethylammonium chloride | 1% |
| Hydroxypropyl guar | 0.5% |
| Glyceryl stearate | 1% |
| Polyvinylpyrrolidone | 2% |
| Preserving agents | qs % |
| Water | qs 100% |

[1] Vinylpyrrolidone/dimethylaminopropylmethacrylamide/lauryldimethylmethacrylamidopropylammonium chloride terpolymer, sold by the company ISP under the name Styleze W20

| Composition B | |
|---|---|
| Styleze W20 [1] | 4% |
| Cetearyl alcohol | 4% |
| Glycerol | 5% |
| Amodimethicone (DC 939) | 1.5% |
| Behenyltrimethylammonium chloride | 1% |
| Preserving agents | qs % |
| Water | qs 100% |

[1] Vinylpyrrolidone/dimethylaminopropylmethacrylamide/lauryldimethylmethacrylamidopropylammonium chloride terpolymer, sold by the company ISP under the name Styleze W20

| Composition C | |
|---|---|
| Styleze W20 [1] | 5% |
| Cetearyl alcohol | 4% |
| Amodimethicone (DC 939) | 1.5% |
| Behenyltrimethylammonium chloride | 1% |
| Laureth-4 | 1% |
| Mineral oil | 1% |
| Preserving agents | qs % |
| Water | qs 100% |

[1] Vinylpyrrolidone/dimethylaminopropylmethacrylamide/lauryldimethylmethacrylamidopropylammonium chloride terpolymer, sold by the company ISP under the name Styleze W20

| Composition D | |
|---|---|
| Styleze W20 [1] | 1% |
| Cetyl alcohol | 4% |
| Amodimethicone (DC 939) | 1% |
| Cetyltrimethylammonium chloride | 1% |
| Dimethiconol (DC 1501 fluid) | 2% |
| Preserving agents | qs % |
| Water | qs 100% |

[1] Vinylpyrrolidone/dimethylaminopropylmethacrylamide/lauryldimethylmethacrylamidopropylammonium chloride terpolymer, sold by the company ISP under the name Styleze W20

The percentages of each of the compounds in the cosmetic compositions according to the present disclosure were calculated by weight of active material relative to the total weight of the compositon.

Compositions (A) to (D) were applied to European hair.

It was observed that the compositions in accordance with the disclosure made it possible to substantially reduce the volume of frizzy hair, while at the same time giving the hair good cosmetic properties, such as a satisfactory feel.

What is claimed is:

1. A cosmetic composition for treating keratin fibers, comprising, in a cosmetically acceptable medium:
at least one cationic poly(vinyllactam) polymer comprising:
a) at least one monomer chosen from vinyllactam and alkylvinyllactam monomers;
b) at least one monomer chosen from those of (Ia) and (Ib):

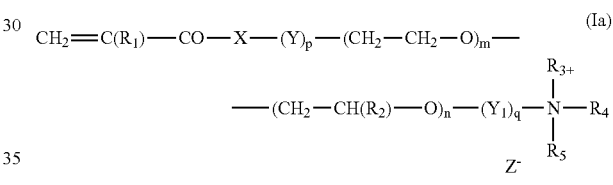

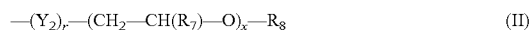

wherein:
X is chosen from an oxygen atom and radicals $NR_6$,
$R_1$ and $R_6$, independently of each other, are chosen from hydrogen atoms and linear and branched $C_1$-$C_5$ alkyl radicals,
$R_2$ are chosen from linear and branched $C_1$-$C_4$ alkyl radicals,
$R_3$, $R_4$ and $R_5$, independently of each other, are chosen from hydrogen atoms, linear and branched $C_1$-$C_{30}$ alkyl radicals, and radicals of formula (II):

$$-(Y_2)_r-(CH_2-CH(R_7)-O)_x-R_8 \quad (II)$$

Y, $Y_1$ and $Y_2$, independently of each other, are chosen from linear and branched $C_2$-$C_{16}$ alkylene radicals,
$R_7$ is chosen from a hydrogen atom, liner and branched $C_1$-$C_4$ alkyl radicals and linear and branched $C_1$-$C_4$ hydroxyalkyl radicals,
$R_8$ is chosen from a hydrogen atom and linear and branched $C_1$-$C_{30}$ alkyl radicals, p, q and r, independently of each other, are chosen from the value 0 or the value 1, m and n, independently of each other, are integers ranging from 0 to 100,
X is an integer ranging from 1 to 100, and Z is an anion chosen from organic and mineral acid anions;
with the proviso that:
at least one of the substituents $R_3$, $R_4$, $R_5$ or $R_8$ is chosen from linear and branched $C_9$-$C_{30}$ alkyl radicals,
if m or n is other than zero, then q is equal to 1, and
if m or n is equal to zero, then p or q is equal to 0;
cetearyl alcohol, and
at least one amino silicone.

2. The cosmetic composition according to claim 1, wherein the at least one monomer chosen from vinyllactam and alkylvinyllactam monomers is a compound of structure (III):

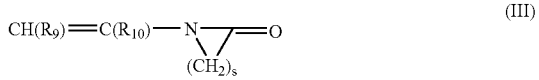

wherein:
s is an integer ranging from 3 to 6,
$R_9$ is chosen from a hydrogen atom and $C_1$-$C_5$ alkyl radicals, and
$R_{10}$ is chosen form a hydrogen atom and $C_1$-$C_5$ alkyl radicals;
with the proviso that at least one of the radicals $R_9$ and $R_{10}$ is a hydrogen atom.

3. The cosmetic composition according to claim 2, wherein the at least one monomer of formula (III) is vinylpyrrolidone.

4. The cosmetic composition according to claim 1, wherein, the radicals $R_3$, $R_4$ and $R_5$, independently of each other, are chosen from hydrogen atoms and linear and branched $C_1$-$C_{30}$ alkyl radicals.

5. The cosmetic composition according to claim 1, wherein the at least one monomer chosen from those of (Ia) and (Ib) is a monomer of formula (Ia).

6. The cosmetic composition according to claim 5, wherein, m and n are equal to zero.

7. The cosmetic composition according to claim 1, wherein Z is chosen from halide ions, phosphate ions, a methosulfate ion and a tosylate ion.

8. The cosmetic composition according to claim 1, wherein the at least one cationic poly(vinyllactam) polymer comprises at least one additional monomer chosen from cationic and nonionic monomer.

9. The cosmetic composition according to claim 8, wherein the at least one cationic poly(vinyllactam) is a terpolymer comprising:
(a) one monomer of formula (III):

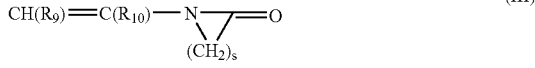

wherein:
s is an integer ranging from 3 to 6,
$R_9$ is chosen from a hydrogen atom and $C_1$-$C_5$ alkyl radicals, and
$R_{10}$ is chosen from a hydrogen atom and $C_1$-$C_5$ alkyl radicals;
with the proviso that at least one of the radicals $R_9$ and $R_{10}$ is a hydrogen atom,
(b) one monomer of formula (Ia) wherein p=1, q=0, $R_3$ and $R_4$, independently of each other, are chosen from hydrogen atoms and $C_1$-$C_5$ alkyl radicals and $R_5$ is chosen from $C_9$-$C_{24}$ alkyl radicals, and (c) one monomer of formula (Ib) wherein $R_3$ and $R_4$, independently of each other, are chosen from hydrogen atoms and $C_1$-$C_5$ alkyl radicals.

10. The cosmetic composition according to claim 9, wherein the terpolymer comprises, by weight 40% to 95% of monomer (a), 0.25% to 50% of monomer (b) and 0.1% to 55% of monomer (c).

11. The composition according to claim 1, wherein the at least one cationic poly(vinyllactam) polymer is chosen from vinylpyrrolidone/dimethyl -aminopropylmethacrylamide/ dodecyldimethylmethacrylamidopropylammonium tosylate terpolymers, vinylpyrrolidone/dimethylaminopropylmethacrylamide/cocoyl -dimethylmethacrylamidopropylammonium tosylate terpolymers and vinylpyrrolidone/dimethylaminopropylmethacrylamide/ lauryldimethylmethacrylamidopropyl -ammonium chloride terpolymers.

12. The composition according to claim 11, wherein the at least one cationic poly(vinyllactam) polymer is a vinylpyrrolidone/dimethylaminopropyl methacrylamide/lauryldimethylmethacrylamidopropylammonium chloride terpolymer.

13. The composition according to claim 1, wherein the weight-average molecular mass of the at least one cationic poly(vinyllactam) polymer ranges from 500 to 20,000,000.

14. The cosmetic composition according to claim 13, wherein the weight-average molecular mass of the at least one cationic poly(vinyllactam) polymer ranges from 400,000 to 800,000.

15. The cosmetic composition according to claim 1, wherein the at least one cationic poly(vinyllactam) polymer is present in an amount ranging from 0.05% to 30% by weight relative to the total weight of the composition.

16. The cosmetic composition according to claim 15, wherein the at least one cationic poly(vinyllactam) polymer is present in an amount ranging for 0.2% to 10% by weight relative to the total weight of the composition.

17. The cosmetic composition according to claim 1, wherein the at least one linear or branched saturated fatty alcohol is solid or pasty at 25° C.

18. The cosmetic composition according to claim 1, wherein the at least one linear or branched saturated fatty alcohol is present in an amount ranging from 0.1% to 30% by weight relative to the total weight of the composition.

19. The cosmetic composition according to claim 18, wherein the at least one linear or branched saturated fatty alcohol is present in an amount ranging 0.5% to 10% by weight relative to the total weight of the composition.

20. The cosmetic composition according to claim 1, wherein the at least one amino silicone is chosen from:
(a) compounds of formula (V):

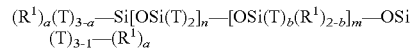

wherein:
T is chosen from a hydrogen atom, a phenyl radical, a hydroxyl radical, $C_1$-$C_8$ alkyl radicals, and $C_1$-$C_8$ alkoxy radicals,
a is an integer ranging from 0 to 3,
b is 0 or 1,
m and n are numbers such that the sum (n +m) ranges from 1 to 2000, n is a number ranging from 0 to 1999, and m is a number ranging from 1 to 2000;
$R^1$ is chosen from monovalent radicals of formula —$C_qH_{2q}$L wherein q is a number ranging from 2 to 8 and L is an optionally quaternized amino group chosen from:

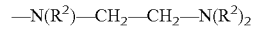

—N($R^2$)$_2$

—N$^⊕$($R^2$)$_3$Q$^-$

—N$^⊕$($R^2$)(H)$_2$Q$^-$

—N$^⊕$($R^2$)$_2$HQ$^-$

—N($R^2$)—CH$_2$—CH$_2$—N$^⊕$($R^2$)(H)$_2$Q$^-$ wherein $R^2$ is chosen from a hydrogen atom, a phenyl radical, a benzyl radical, and saturated monovalent hydrocarbon-based radicals, and $Q^{31}$ is a halide ion, (b) compounds of formula (VII):

$$R^3-\underset{R^3}{\underset{|}{Si}}-O-\left[\underset{R^3}{\underset{|}{\overset{R^3}{\overset{|}{Si}}}}-O\right]_r\left[\underset{R^3}{\underset{|}{\overset{R^4-CH_2-CHOH-CH_2-N^+(R^3)_3Q^-}{\overset{|}{Si}}}}-O\right]_s \underset{R^3}{\underset{|}{\overset{R^3}{\overset{|}{Si}}}}-R^3 \qquad (VII)$$

wherein:
- $R^3$ is chosen from monovalent $C_1$-$C_{18}$ hydrocarbon-based radicals,
- $R^4$ is chosen from divalent hydrocarbon-based radicals;
- Q$^-$ is a halide ion;
- R has an average statistical value ranging from 2 to 20;
- S has an average statistical value ranging from 20 to 200, (c) quaternary ammonium silicones of formula (XII);

$$R_8-\underset{R_7}{\underset{|}{\overset{R_7}{\overset{|}{N^+}}}}-CH_2-\underset{}{\overset{OH}{\overset{|}{CH}}}-CH_2-R_6-\underset{R_7}{\underset{|}{\overset{R_7}{\overset{|}{Si}}}}-O-\left[\underset{R_7}{\underset{|}{\overset{R_7}{\overset{|}{Si}}}}-R_6-CH_2-CHOH-CH_2-\underset{R_7}{\underset{|}{\overset{R_7}{\overset{|}{N^+}}}}-R_8\right] \qquad 2X^- \quad (XII)$$

wherein:
- $R_7$, which may be identical or different, are chosen from monovalent hydrocarbon-based radicals containing from 1 to 18 carbon atoms;
- $R_6$ is chosen from divalent hydrocarbon-based radicals;
- $R_8$, which may be identical or different, are chosen from hydrogen atoms and monovalent hydrocarbon-based radicals containing from 1 to 18 carbon atoms;
- $X^{31}$ is an anion;
- R has a mean statistical value ranging from 2 to 200, (d) amino silicones of formula (XIII):

$$\underset{\underset{NH_2}{\underset{|}{(C_mH_{2m})}}}{\underset{|}{\underset{NH}{\underset{|}{(C_nH_{2n})}}}}{\underset{|}{Si}}-\left[O-\underset{R_2}{\underset{|}{\overset{R_1}{\overset{|}{Si}}}}-O-\underset{R_4}{\underset{|}{\overset{R_3}{\overset{|}{Si}}}}-R_5\right]_3 \qquad (XIII)$$

wherein:
- $R_1$, $R_2$, $R_3$ and $R_4$, which may be identical or different, are chosen from $C_1$-$C_4$ alkyl radicals and phenyl groups,
- $R_5$ is chosen from $C_1$-$C_4$ alkyl radicals and a hydroxyl group,
- n is an integer ranging from 1 to 5,
- m is an integer ranging from 1 to 5, and wherein x is chosen such that the amine number ranges from 0.01 to 1 meq/g.

21. The cosmetic composition according to claim 20, wherein the at least one amino silicone of formula (V) is trimethylsilylamodimethicone, of formula (VI):

$$(CH_3)_3SiO-\left[\underset{CH_3}{\underset{|}{\overset{CH_3}{\overset{|}{Si}}}}O\right]_n\left[\underset{\underset{\underset{NH_2}{\underset{|}{(CH_2)_2}}}{\underset{|}{NH}}}{\underset{|}{\underset{CH_2}{\underset{|}{CHCH_3}}}}\underset{|}{\overset{CH_3}{\overset{|}{Si}}}O\right]_m -Si(CH_3)_3 \qquad (VI)$$

wherein
- n is an integer ranging from 1 to 5, and
- m is an integer ranging from 1 to 5.

22. The cosmetic composition according to claim 1, wherein the at least one amino silicone is present in an amount ranging from 0.01% to 20% by weight relative to the total weight of the composition.

23. The cosmetic composition according to claim 22, wherein the at least one amino silicone is present in an amount ranging from 0.1% to 5% by weight relative to the total weight of the composition.

24. The cosmetic composition according to claim 1, further comprising at least one oxyalkylenated silicone.

25. The cosmetic composition according to claim 24, wherein the at least one oxyalkylenated silicone is chosen from compounds of formulae (XIV), (XV), (XVI), (XVII) and (XVIII):

$$R_2-\underset{CH_3}{\underset{|}{\overset{CH_3}{\overset{|}{Si}}}}-O-\left[\underset{R_1}{\underset{|}{\overset{CH_3}{\overset{|}{Si}}}}-O\right]_o\left[\underset{R_2}{\underset{|}{\overset{CH_3}{\overset{|}{Si}}}}-O\right]_m\left[\underset{CH_3}{\underset{|}{\overset{CH_3}{\overset{|}{Si}}}}-O\right]_n\underset{CH_3}{\underset{|}{\overset{CH_3}{\overset{|}{Si}}}}-R_2 \qquad (XIV)$$

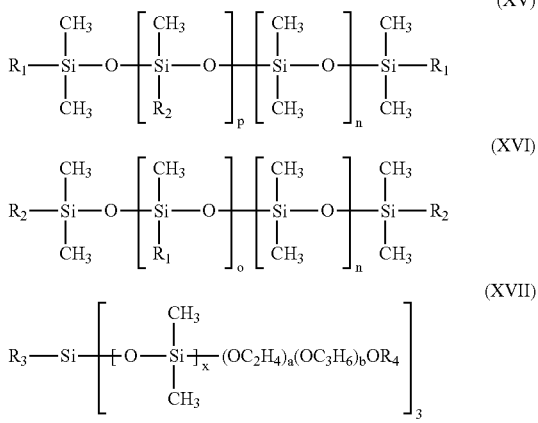

wherein:
R$_1$, which may be identical or different, is chosen from linear and branched C$_1$-C$_{30}$ alkyl and phenyl radicals,
R$_2$, which may be identical or different, is chosen from radicals
C$_c$H$_{2c}$—O—(C$_2$H$_4$O)$_a$(C$_3$H$_6$O)$_b$—R$_5$ and radicals —C$_c$H$_{2c}$—O—(C$_4$H$_8$O)$_a$—R$_5$,
R$_3$ and R$_4$, which may be identical or different, are chosen from linear and branched C$_1$ to C$_{12}$ alkyl radicals,
R$_5$, which may be identical or different, is chosen from a hydrogen atom, linear and branched alkyl radicals containing from 1 to 12 carbon atoms, linear and branched alkoxy radicals containing from 1 to 6 carbon atoms, linear and branched acyl radicals containing from 2 to 30 carbon atoms, a hydroxyl radical, —SO$_3$M radicals, C$_1$-C$_6$ aminoalkoxy radicals optionally substituted on the amine, C$_2$-C$_6$ aminoacyl radicals optionally substituted on the amine, —NHCH$_2$CH$_2$COOM radicals, —N(CH$_2$CH$_2$COOM)$_2$ radicals, aminoalkyl radicals optionally substituted on the amine and on the alkyl chain C$_2$-C$_{30}$ carboxyacyl radicals, groups optionally substituted with one or two substituted aminoalkyl radicals,—CO(CH$_2$)$_d$COOM radicals, —COCHR$_7$(CH$_2$)$_d$COOM radicals, —NHCO(CH$_2$)$_d$OH radicals, —NH$_3$Y radicals, and a phosphate group,
M, which may be identical or different, is chosen from a hydrogen atom, Na, K, Li, NH$_4$ and organic amines,
R$_7$ is chosen from a hydrogen atom and radicals —SO$_3$M,
d ranges from 1 to 10,
m ranges from 0 to 20,
n ranges from 0 to 500,
o ranges from 0 to 20,
p ranges from 1 to 50,
a ranges from 0 to 50,
b ranges from 0 to 50,
a +b is greater than or equal to 2,
c ranges from 0 to 4,
x ranges from 1 to 100,
Y is chosen from monovalent mineral and organic anions, with the proviso that when the at least one oxyalkylenated silicone is of formula (XV) and R$_5$ is hydrogen, then n is greater than 12;

([Z(R$_2$SiO)$_q$R'$_2$SiZO][(C$_n$H$_{2n}$O)$_r$])$_s$ (XVIII)

wherein in formula (XVIII):
R$_2$ and R'$_2$, which may be identical or different, are chosen from monovalent C$_1$-C$_{30}$ hydrocarbon-based radicals,
n is an integer ranging from 2 to 4,
q is a number greater than or equal to 4,
r is a number greater than or equal to 4,
s is a number greater than or equal to 4,
Z is chosen from divalent organic groups linked to the adjacent silicon atom via a carbon-silicon bond and to the polyoxyalkylene block (C$_n$H$_{2n}$O) via an oxygen atom,
wherein the average molecular weight of each siloxane block ranges from 400 to 10,000, and the average molecular weight of each polyoxyalkylene block ranges from 300 to 10,000,
wherein the siloxane blocks are present in an amount ranging from 10% to 95% by weight of the block copolymer,
wherein the number-average molecular weight of the block copolymer ranges from 2500 to 1,000,000.

26. The cosmetic composition according to claim 1, further comprising at least one silicone chosen from silicone gums.

27. The cosmetic composition according to claim 26, wherein the at least one silicone gum is chosen from polyorganosiloxanes with number-average molecular masses ranging from 200,000 to 1,000,000, used alone or in the form of a mixture in a solvent.

28. The cosmetic composition according to claim 26, wherein the at least one silicone gum, along or in the form of a mixture, is chosen from:
polydimethylsiloxane,
polydimethylsiloxane/methylvinylsiloxane gums,
polydimethy7lsiloxane/diphenylsiloxane,
polydimethylsiloxane/phenylmethylsiloxane,
polydimethylsiloxane/diphenylsiloxane/methylvinylsiloxane and the following mixtures:
mixtures formed from a polydimethylsiloxane hydroxylated at the end of the chain and of a cyclic polydimethylsiloxane;
mixtures formed from a polydimethylsiloxane gum and a cyclic silicone; and
mixtures of polydimethylsiloxanes of different viscosities.

29. The cosmetic composition according to claim 1, further comprising at least one additional fixing polymer.

30. The cosmetic composition according to claim 1, further comprising at least one rheology modifier.

31. The cosmetic composition according to claim 1, further comprising at least one cosmetic adjuvant chosen from cationic, anionic, amphoteric and nonionic surfactants; silicones other than the at least one amino silicone; conditioning agents of ester type; antifoams; moisturizers; emollients; plasticizers; water-soluble and liposoluble, silicone-based and non-silicone-based sunscreens; permanent and temporary dyes; fragrances; peptizers; preserving agents ceramides; pseudoceramides; vitamins and provitamins; panthenol; proteins; sequestrants; solubilizers; basifying agents; anticorrosion agents; fatty substances; plant oils; animal oils; mineral oils; synthetic oils; reducing agents; antioxidants; and oxidizing agents.

32. The cosmetic composition according to claim 31, wherein the at least one cosmetic adjuvant is present in an amount ranging from 0.001% to 50% by weight relative to the total weight of the composition.

33. The cosmetic composition according to claim 1, wherein the cosmetically acceptable medium is chosen from aqueous, alcoholic, and aqueous-alcoholic mediums.

34. The cosmetic composition according to claim 32, wherein the aqueous-alcoholic medium comprises at least one alcohol chosen from C$_1$-C$_4$ lower alcohols, polyols, and polyol monoethers.

35. The cosmetic composition according to claim 33, wherein the at least one alcohol is ethanol.

36. The cosmetic composition according to claim 1, wherein it is in the form of a cream, a mousse, a lotion, a gel, a spray or a hair conditioner.

37. The cosmetic composition according to claim 1, it is packaged in a vaporizer, a pump-dispenser bottle or an aerosol device.

38. The cosmetic composition according to claim 36, it is packaged in an aerosol device.

39. The cosmetic composition according to claim 37, further comprising at least one propellant chosen from air, nitrogen, carbon dioxide, dimethyl ether, $C_3$-$C_5$ alkanes and 1,1-difluoroethane.

40. An aerosol device, comprising:
a container comprising a composition, wherein the composition comprises, in a cosmetically acceptable medium:
at least one cationic poly(vinyllactam) polymer comprising:
a) at least one monomer chosen from vinyllactam and alkylvinyllactam monmers;
b) at least one monomer chosen from those of formulae (Ia) and (Ib):

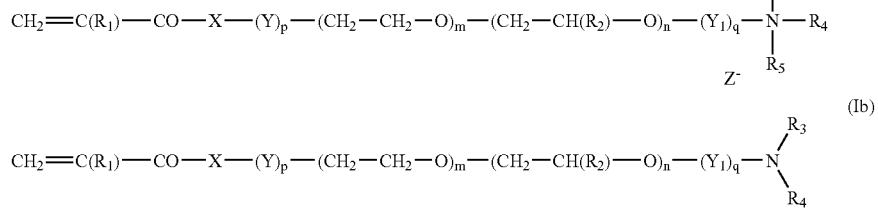

wherein:

X is chosen from an oxygen atom and radicals $NR_6$, $R_1$ and $R_6$, independently of each other, are chosen from hydrogen atoms and linear and branched $C_1$-$C_5$ alkyl radicals, $R_2$ are chosen from linear and branched $C_1$-$C_4$ alkyl radicals, $R_3$, $R_4$ and $R_5$, independently of each other, are chosen from hydrogen atoms, linear and branched $C_1$-$C_{30}$ alkyl radicals, and radicals of formula (II):

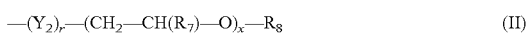

$Y, Y_1$ and $Y_2$, independently of each other, are chosen from linear and branched $C_2$-$C_{16}$ alkylene radicals, $R_7$ is chosen from a hydrogen atom, linear and branched $C_1$-$C_4$ alkyl radicals, and linear and branched $C_1$-$C_4$ hydroxyalkyl radicals, $R_8$ is chosen from a hydrogen atom and linear and branched $C_1$-$C_{30}$ alkyl radicals, P, q and r, independently of each other, are chosen from the value 0 or the value 1, m and n, independently of each other, are integers ranging from 0 to 100, x is an integer ranging from 1 to 100, and Z is chosen from organic and mineral acid anions;

with the proviso that:
at least one of the substituents $R_3$, $R_4$, $R_5$ or $R_8$ is chosen from linear and branched $C_9$-$C_{30}$ alkyl radicals,
if m or n is other than zero, then q is equal to 1, and
if m or n is equal to zero, then p or q is equal to 0;
cetearyl alcohol,
at least one amino silicone; and
at least one propellant
and an appropriate device for distributing the composition.

41. A cosmetic treatment process for keratin fibers, comprising:

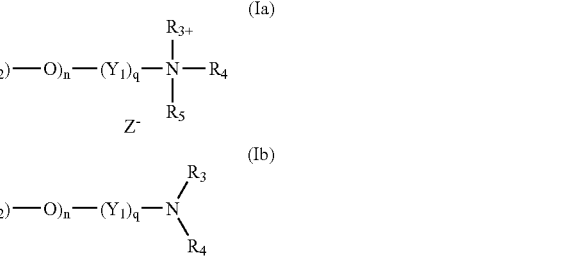

applying a cosmetic composition onto keratin fibers, wherein the composition comprises, in a cosmetically acceptable medium:
at least one cationic poly(vinyllactam) polymer comprising:
a) at least one monomer chosen from vinyllactam and alkylvinyllactam monomers;
b) at least one monomer chosen from those of formulae (Ia) and (Ib):

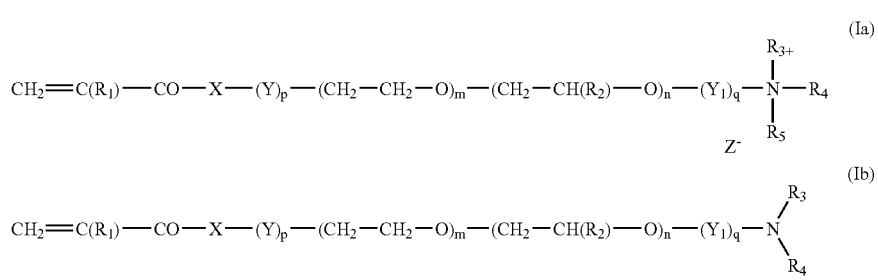

wherein:

X is chosen from an oxygen atom and radicals $NR_6$, $R_1$ and $R_6$, independently of each other, are chosen from hydrogen atoms and linear and branched $C_1$-$C_5$ alkyl radicals, $R_2$ are chosen from linear and branched $C_1$-$C_4$ alkyl radicals, $R_3$, $R_4$ and $R_5$, independently of each other, are chosen from hydrogen atoms, linear and branched $C_1$-$C_{30}$ alkyl radicals, and radicals of formula (II):

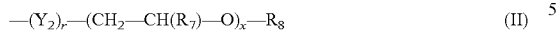

(II)

$Y$, $Y_1$ and $Y_2$, independently of each other, are chosen from linear and branched $C_2$-$C_{16}$ alkylene radicals, $R_7$ is chosen from a hydrogen atom, linear and branched $C_1$-$C_4$ alkyl radicals, and linear and branched $C_1$-$C_4$ hydroxyalkyl radicals, $R_8$ is chosen from a hydrogen atom and linear and branched $C_1$-$C_{30}$ alkyl radicals, p, q and r, independently of each other, are chosen from the value 0 or the value 1, m and n, independently of each other, are integers ranging from 0 to 100, x is an integer ranging from 1 to 100, and Z is chosen from organic and mineral acid anions;
with the proviso that:
  at least one of the substituents $R_3$, $R_4$, $R_5$ or $R_8$ is chosen from linear and branched $C_9$-$C_{30}$ alkyl radicals,
  if m or n is other than zero, then q is equal to 1, and
  if m or n is equal to zero, then p or q is equal to 0;
cetearyl alcohol, and
at least one amino silicone.

42. The cosmetic treatment process according to claim 40, wherein the application of the composition is not followed by rinsing.

43. A process for caring for hair, comprising:
applying a cosmetic composition to the hair, wherein the composition comprises, in a cosmetically acceptable medium:
at least one cationic poly(vinyllactam) polymer comprising:
  a) at least one monomer chosen from vinyllactam and alkylvinyllactam monomers;
  b) at least one monomer chosen from those of formulae (Ia) and (Ib):

wherein:
  X is chosen from an oxygen atom and radicals $NR_6$,
  $R_1$ and $R_6$, independently of each other, are chosen from hydrogen atoms and linear and branched $C_1$-$C_5$ alkyl radicals,
  $R_2$ are chosen from linear and branched $C_1$-$C_4$ alkyl radicals,
  $R_3$, $R_4$ and $R_5$, independently of each other, are chosen from hydrogen atoms, linear and branched $C_1$-$C_{30}$ alkyl radicals, and radicals of formula (II):

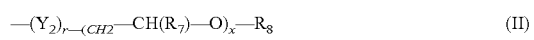

(II)

$Y$, $Y_1$ and $Y_2$, independently of each other, are chosen from linear and branched $C_2$-$C_{16}$ alkylene radicals, $R_7$ is chosen from a hydrogen atom, linear and branched $C_1$-$C_4$ alkyl radicals, and linear and branched $C_1$-$C_4$ hydroxyalkyl radicals, $R_8$ is chosen from a hydrogen atom and linear and branched $C_1$-$C_{30}$ alkyl radicals, p, q and r, independently of each other, are chosen from the value 0 or the value 1, m and n, independently of each other, are integers ranging from 0 to 100, x is an integer ranging from 1 to 100, and Z is chosen from organic and mineral acid anions
;
with the proviso that:
  at least one of the substituents $R_3$, $R_4$, $R_5$ or $R_8$ is chosen from linear and branched $C_9$-$C_{30}$ alkyl radicals,
  if m or n is other than zero, then q is equal to 1, and
  if m or n is equal to zero, than p or q is equal to 0;
cetearyl alcohol, and
at least one amino silicone.

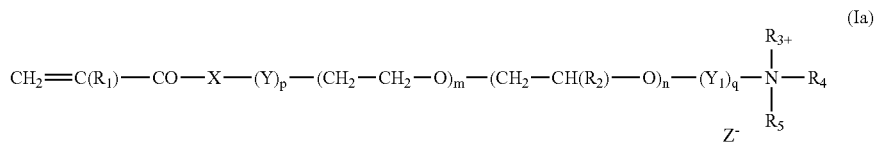

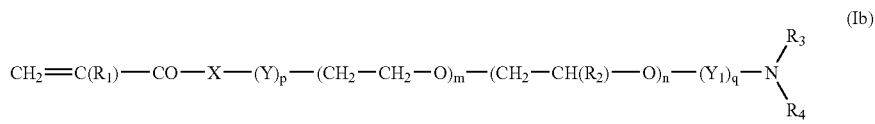

* * * * *

UNITED STATES PATENT AND TRADEMARK OFFICE
CERTIFICATE OF CORRECTION

| | |
|---|---|
| PATENT NO. | : 8,936,779 B2 |
| APPLICATION NO. | : 11/643864 |
| DATED | : January 20, 2015 |
| INVENTOR(S) | : Dorothee Pasquet et al. |

It is certified that error appears in the above-identified patent and that said Letters Patent is hereby corrected as shown below:

In the Claims,

Column 37, line 23, "form" should be -- from --.

Column 39, line 11, "Q31" should be -- Q- --.

Column 39, line 51, "X31" should be -- X- --.

Column 46, line 36, "anions" should be -- anions; --.

Column 46, line 37, the ";" should be deleted.

Column 46, line 45, "than" should be -- then --.

Signed and Sealed this
Fifteenth Day of September, 2015

Michelle K. Lee
*Director of the United States Patent and Trademark Office*